US012589385B2

(12) United States Patent
Ikuta et al.

(10) Patent No.: US 12,589,385 B2
(45) Date of Patent: Mar. 31, 2026

(54) PHOTOCATALYTIC FILTER AND DEODORIZING APPARATUS

(71) Applicant: NBC Meshtec Inc., Tokyo (JP)

(72) Inventors: Hiromi Ikuta, Tokyo (JP); Yusei Matsumoto, Tokyo (JP); Yohei Jikihara, Tokyo (JP); Takanori Matsumoto, Tokyo (JP)

(73) Assignee: NBC Meshtec Inc., Tokyo (JP)

( * ) Notice: Subject to any disclaimer, the term of this patent is extended or adjusted under 35 U.S.C. 154(b) by 437 days.

(21) Appl. No.: 18/030,084

(22) PCT Filed: Oct. 7, 2021

(86) PCT No.: PCT/JP2021/037178
§ 371 (c)(1),
(2) Date: Apr. 4, 2023

(87) PCT Pub. No.: WO2022/075416
PCT Pub. Date: Apr. 14, 2022

(65) Prior Publication Data
US 2023/0372919 A1 Nov. 23, 2023

(30) Foreign Application Priority Data
Oct. 8, 2020 (JP) ................................. 2020-170238

(51) Int. Cl.
A61L 9/20 (2006.01)
B01J 21/06 (2006.01)
(Continued)

(52) U.S. Cl.
CPC ............... B01J 35/39 (2024.01); A61L 9/205 (2013.01); B01J 21/063 (2013.01); B01J 35/40 (2024.01); B01J 35/45 (2024.01); A61L 2101/02 (2020.08); A61L 2202/13 (2013.01); A61L 2209/14 (2013.01); B01J 35/56 (2024.01); B82Y 30/00 (2013.01)

(58) Field of Classification Search
CPC ... B01J 35/39; B01J 35/40; B01J 35/45; B01J 21/063; A61L 9/205
See application file for complete search history.

(56) References Cited

U.S. PATENT DOCUMENTS

2009/0162251 A1   6/2009   Lai et al.
2021/0139341 A1   5/2021   Baldi et al.
2022/0388860 A1   12/2022   Baldi et al.

FOREIGN PATENT DOCUMENTS

CA   3062596 A1   11/2018
CN   1724143 A   1/2006
(Continued)

OTHER PUBLICATIONS

Machine translation of JP 2012192323 (Year: 2012).*
(Continued)

*Primary Examiner* — Timothy C Cleveland
(74) *Attorney, Agent, or Firm* — Dickinson Wright PLLC

(57) ABSTRACT
A photocatalytic filter includes a filter substrate, the filter substrate being a porous metal, and a photocatalyst fixed to the filter substrate. When a thickness of the porous metal is t (mm) and an average cell number per inch of the porous metal is C (ppi), a product ($t \times C$) of the thickness t and the average cell number C is from 100 or more to 400 or less.

9 Claims, 10 Drawing Sheets

(51) Int. Cl.

| | |
|---|---|
| *B01J 35/39* | (2024.01) |
| *B01J 35/40* | (2024.01) |
| *B01J 35/45* | (2024.01) |
| *A61L 101/02* | (2006.01) |
| *B01J 35/56* | (2024.01) |
| *B82Y 30/00* | (2011.01) |

(56)         References Cited

FOREIGN PATENT DOCUMENTS

| CN | 1772383 | A | 5/2006 |
|---|---|---|---|
| CN | 110248828 | A | 9/2019 |
| CN | 110944749 | A | 3/2020 |
| JP | 2006000366 | A | 1/2006 |
| JP | 2007083195 | A | 4/2007 |
| JP | 2007275292 | A | 10/2007 |
| JP | 2012050979 | A | 3/2012 |
| JP | 2012192323 | A | 10/2012 |
| JP | 2018167151 | A | 11/2018 |
| JP | 2020506769 | A | 3/2020 |
| KR | 20160098631 | A | 8/2016 |
| WO | 2018207107 | A1 | 11/2018 |

OTHER PUBLICATIONS

Zhu Huitian et al., "Automobile electronic control and new device maintenance technology," published Mar. 31, 2010 (12 pages).
Japan Patent Office, Tokyo, Japan, International Search Report of International Application No. PCT/JP2021/037178, Mailed Dec. 21, 2021, 3 pages.
Zhu, Zhi Yao et al., "Foamed Metal, the Brother of Foam Plastics,"published Apr. 30, 1998.

* cited by examiner

24

1(25)

3(3a)

23

PHOTOCATALYTIC FILTER AND DEODORIZING APPARATUS

CROSS-REFERENCE TO RELATED APPLICATION

The present disclosure is a national stage filing of International Application No. PCT/JP2021/037178 filed on Oct. 7, 2021, designating the United States, which is based on and claims priority to Japanese Patent Application No. 2020-170238, filed on Oct. 8, 2020, the entire disclosures of which are hereby incorporated by reference in their entirety.

TECHNICAL FIELD

The present disclosure relates to a photocatalytic filter and a deodorizing apparatus.

BACKGROUND ART

A deodorizing apparatus that uses a photocatalyst has already been in practical use. The deodorizing apparatus that uses the photocatalyst includes a photocatalytic filter onto which the photocatalyst is supported (or fixed), and a light source that activates the photocatalyst. In the deodorizing apparatus that uses the photocatalyst, the light source is illuminated, the photocatalyst is activated by the light from the light source, and then the gas passes through the photocatalytic filter. Thereby, malodorous components contained in the gas are decomposed by the photocatalyst of the photocatalytic filter (Patent Literature 1: JP 2012-050979 A, for example).

Existing photocatalytic filters have used porous bodies made of ceramic (porous ceramics) for the filter substrate.

SUMMARY

It is regarded that the deodorizing efficiency of the deodorizing apparatus using the photocatalyst is determined by the types of the photocatalyst and the light source to be used. Therefore, materials of the photocatalytic filter (filter substrates) that support the photocatalyst have not been so important. For example, researches such as how the photocatalytic filter material influences the deodorizing effect of the deodorizing apparatus have not been conducted. Subsequently, there is still room for improvement in the filter substrates.

The present disclosure has been made considering the above problem.

A photocatalytic filter includes a filter substrate and a photocatalyst fixed to the filter substrate. The filter substrate is a porous metal. When the thickness of the porous metal is t (mm), and an average cell number per inch of the porous metal is C (ppi), a product (t×C) of the thickness t and the average cell number C is from 100 or more to 400 or less.

DETAILED DESCRIPTION

An embodiment of the present disclosure is explained in detail below with reference to the drawings.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

First Embodiment (Configuration) The configuration of the embodiment is explained below.

Figure 1:
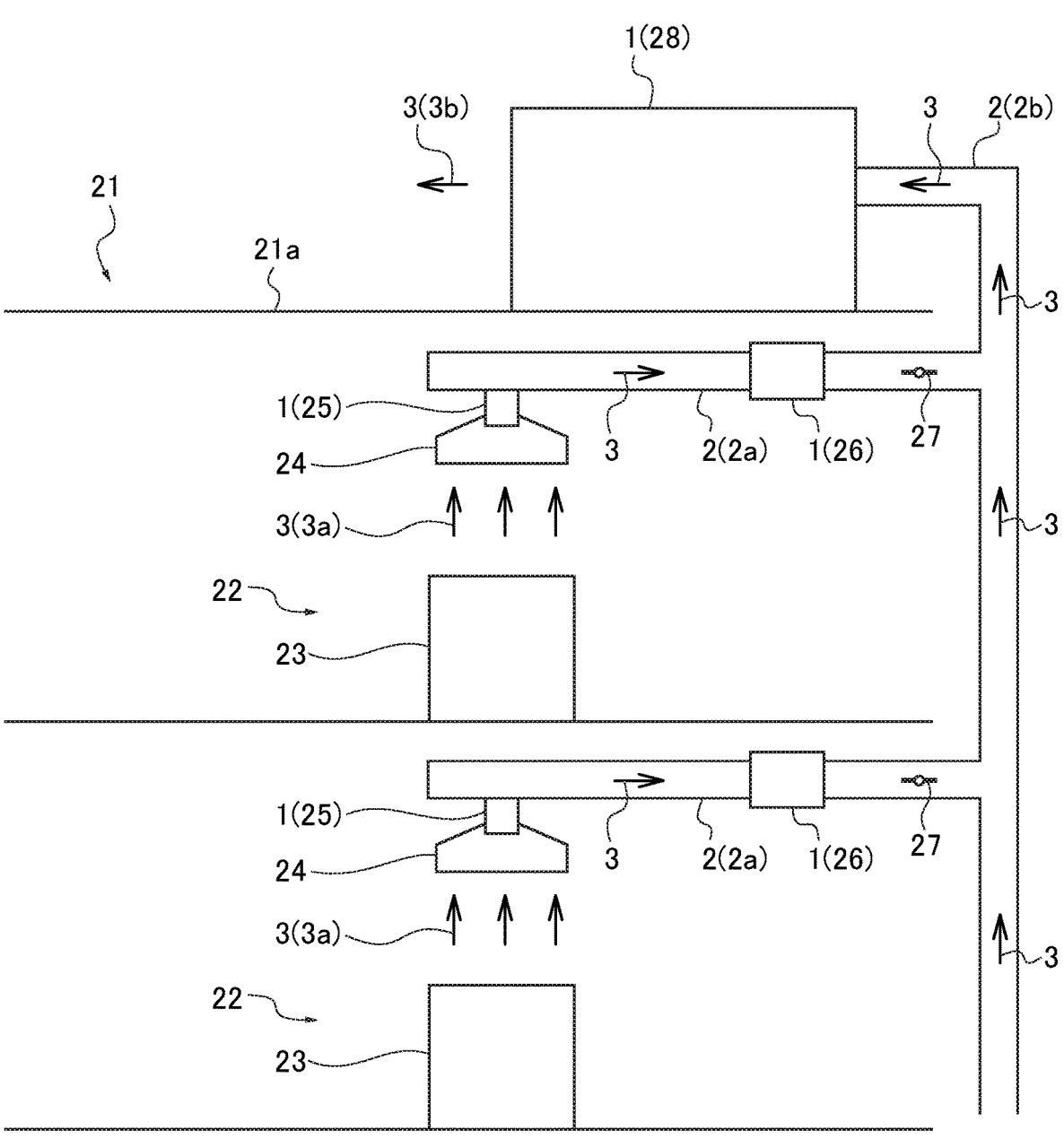
FIG. 1 illustrates a state in which the deodorizing apparatus uses a photocatalytic filter according to an embodiment at a commercial establishment.

As shown in FIG. 1, a deodorizing apparatus 1 is provided at an exhaust path such as an exhaust duct 2, to deodorize gas 3 flowing through the exhaust duct 2. Exhaust gas such as cooking gas flows through the exhaust duct 2 as the gas 3 that is to undergo deodorizing treatment.

Figure 2:
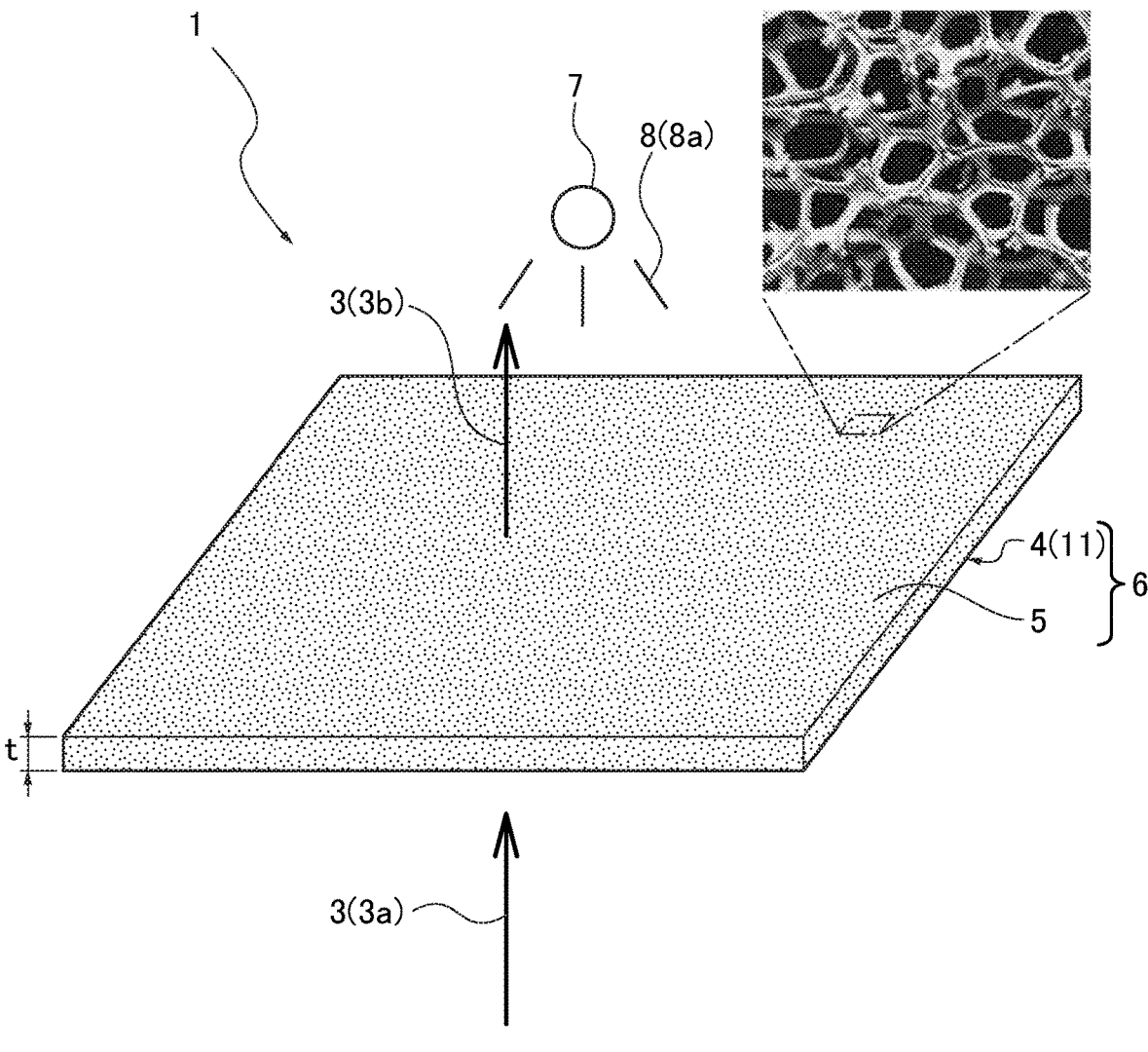
FIG. 2 is a perspective view of the photocatalytic filter according to the embodiment.
Figure 3:
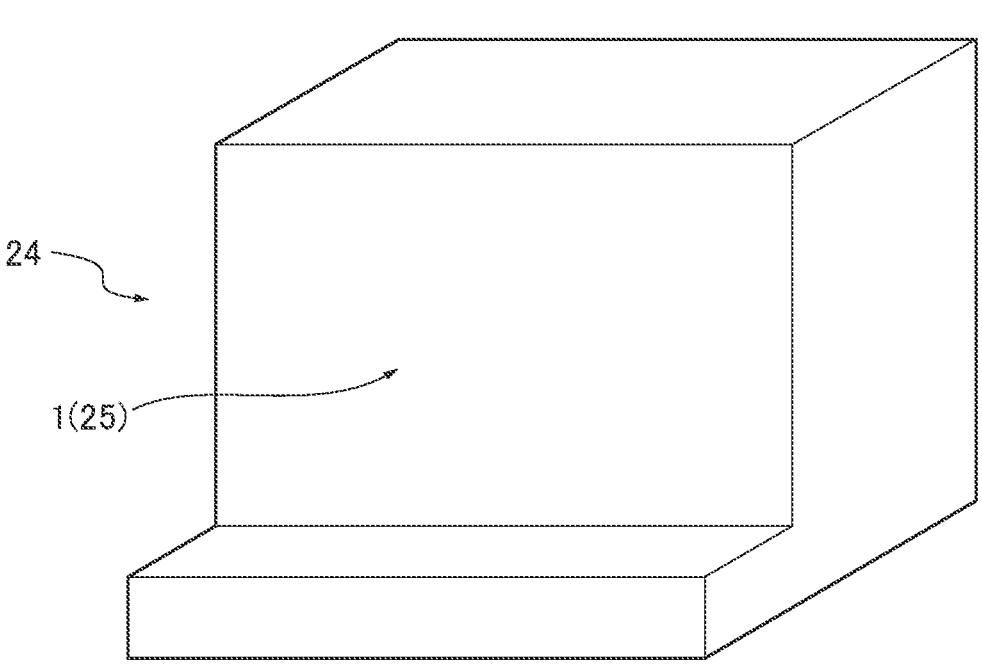
FIG. 3 is a general perspective view of a distributed-type deodorizing apparatus.
Figure 3:
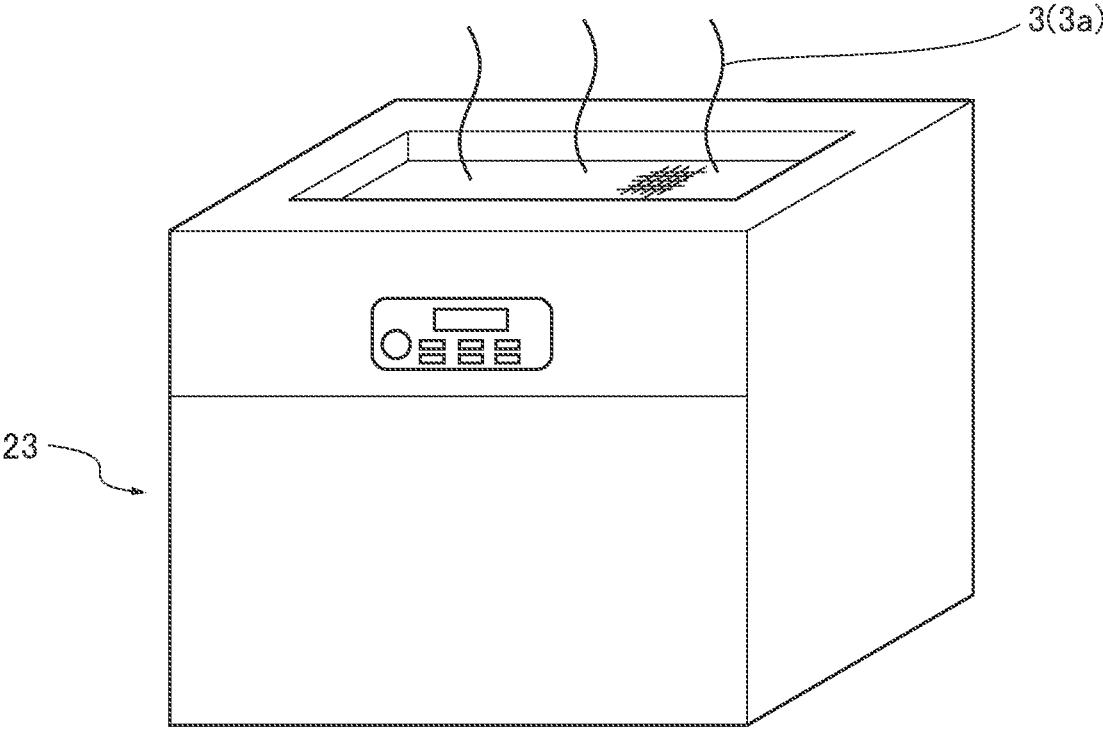
Figure 4:
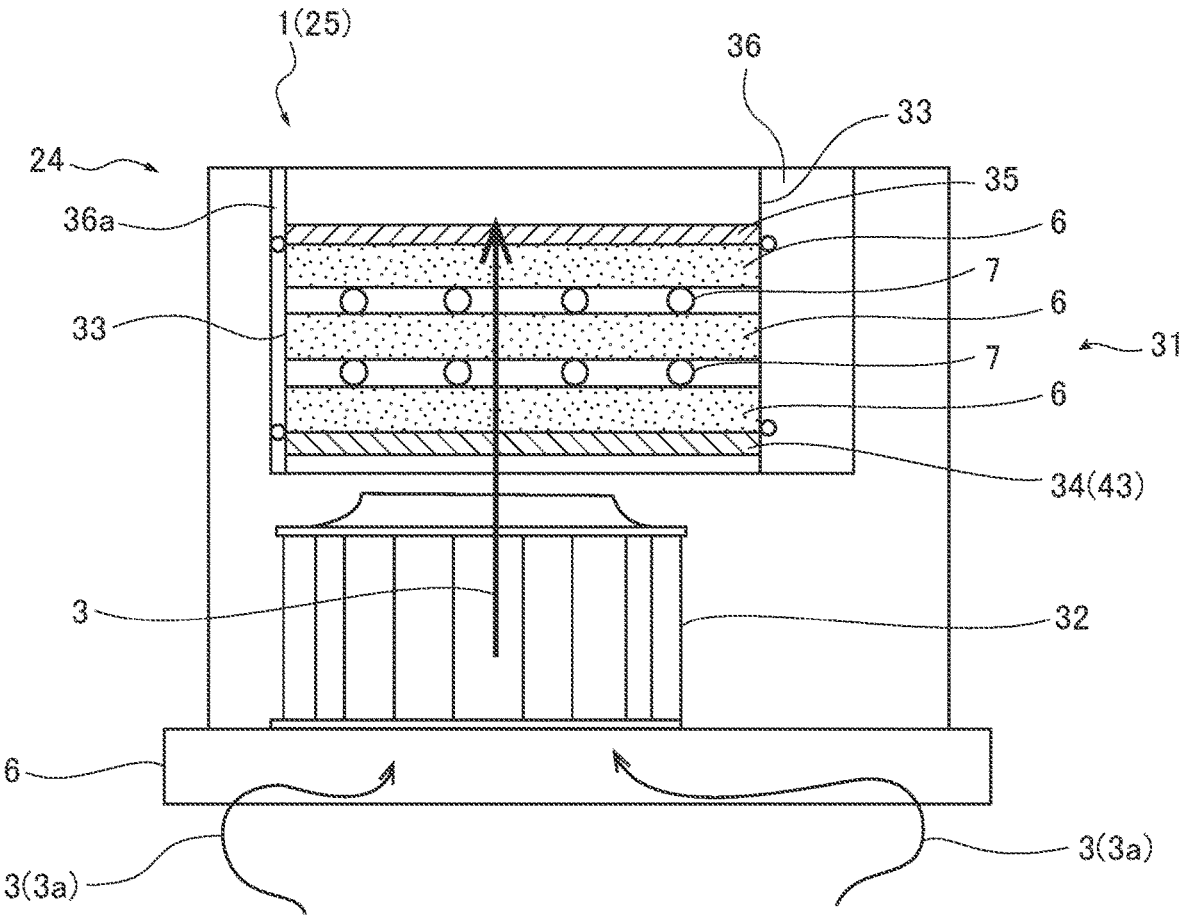
FIG. 4 is a longitudinal cross-sectional view of the distributed-type deodorizing apparatus of FIG. 3.
Figure 4:
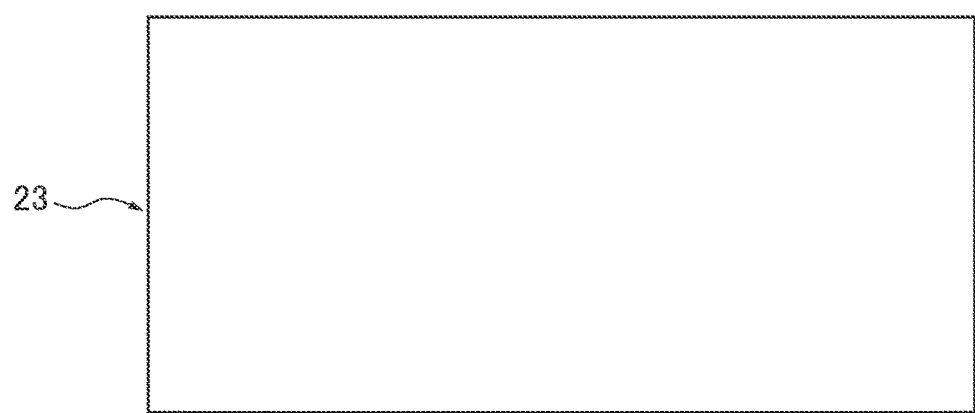

As shown in FIG. 2, the deodorizing apparatus 1 includes a photocatalytic filter 6 and a light source 7. The photocatalytic filter 6 includes a filter substrate 4 and a photocatalyst 5 is supported on (or fixed to) filter substrate 4. The light source 7 activates the photocatalyst 5.

In the deodorizing apparatus 1 that uses the photocatalyst 5, the light source 7 is illuminated and the photocatalyst 5 is activated by the light 8 (primarily ultraviolet light 8a) from the light source 7. In this state, the gas 3 (untreated gas 3a) passes through the photocatalytic filter 6. Thereby, the deodorizing apparatus 1 using the photocatalyst 5 decomposes malodorous components (such as cooking odors) of the gas 3 (into water and carbon dioxide) by the photocatalyst 5 of the photocatalytic filter 6. The cleaned gas 3 from which the malodorous components have been decomposed by the deodorizing apparatus 1 (treated gas 3b) is then discharged into the atmosphere.

Based on the above basic configuration, the below configurations can be provided in the present embodiment.

(1) The photocatalytic filter 6 includes the filter substrate 4 and the photocatalyst 5 fixed to the filter substrate 4. The filter substrate 4 is a porous metal 11. When the thickness of the porous metal 11 is t (mm), and the average cell number per inch of the porous metal 11 is C (ppi), the product (t×C) of the thickness t and the average cell number C is from 100 or more to 400 or less.

The filter substrate 4 is a material (substrate) that constitutes the main body of the photocatalytic filter 6. Fire-resistant material is used for the filter substrate 4.

The photocatalyst 5 is a substance that absorbs the light 8 and exhibits a catalytic function by incurring a chemical reaction on other substances. In this case, the photocatalyst 5 that decomposes at least the malodorous components (other substances) in the untreated gas 3a is used.

The photocatalytic filter 6 is a filter for the deodorization by the photocatalytic reaction of the photocatalyst 5. The photocatalytic reaction is an oxidation-reduction reaction (redox reaction) and the like using the photocatalyst 5 and the light 8. The deodorization is an odor reduction or odor elimination by the decomposition of the malodorous components contained in the gas 3 (untreated gas 3a). In the existing deodorizing apparatus 1, the photocatalytic filter 6 used porous ceramics such as fine ceramics in the filter substrate 4. It is desirable to change such filter substrate to another filter substrate 4 since the porous ceramics are expensive, heavy, and easily broken.

The porous metal 11 is a porous metallic material (material different from porous plates such as perforated plates) that is used as a filter for filtration in various fields such as a filter for industrial use or a filter for cooking food. The porous metal 11 includes microfine three-dimensional continuous air holes, and accordingly, it has much larger porosity compared to porous materials made by sintering metallic fiber or powder (sintered materials), for example. The porous metal 11 having a planar shape (thick planar-shape) has been commercially available. The photocatalytic filter 6 of the present embodiment may use commercially available planar-shaped porous metal 11 as it is or may use one that is machined to be a required shape. The interior structure of the porous portion of the porous metal 11 differs from that of the porous ceramics that have been used as the filter substrate 4. Accordingly, the state of the performance and effect when using the porous metal 11 as the photocatalytic filter 6 is unknown.

The thickness t of the porous metal 11 is a dimension perpendicular to the planar-shaped (rectangular planar-shaped or face-plate shaped) porous metal 11. The gas 3 flows through the porous metal 11 in a direction substantially perpendicular to the inside of the porous metal 11 for a distance of substantially the thickness t portion of the porous metal 11 and passes through the porous metal 11. The thickness t of the porous metal 11 is primarily an indicator relating to the pressure loss of the gas 3.

The average cell number C is a value indicating the density of the cells (air holes) of the porous metal 11. The average cell number C of the porous metal 11 is primarily an indicator relating to the opportunity of contact of the malodorous components with the photocatalyst 5.

According to "Fine ceramics (advanced ceramics, advanced technical ceramics)—Test method for air purification performance of photocatalytic materials—Part 3: Removal of Toluene" (JIS R 1701-3), the test conditions include the flow amount of toluene that is 0.500±0.025 L/min (0° C., 101.3 kPa) at the inlet of a light-irradiating container; the filter size (fine ceramics) that has a width of 49.0±1.0 mm/length of 99.0±1.0 mm; and the illumination intensity of the ultraviolet light 8a at a photocatalytic surface (surface of porous metal 11) that is 10 to 20 W/m². The thickness t and the average cell number C (or density of cells) of the filter are not particularly specified.

Accordingly, there is room for considering conditions such as the thickness t and the average cell number C (or density of cells) of the filter. Conditions such as the thickness t and the average cell number C (or density of cells) of the filter become particularly critical when the porous metal 11 is newly used for the filter substrate 4 of the photocatalytic filter 6.

Thus, the experimentation similar to JIS R 1701-3 was conducted using the existing porous metals 11 under the condition in which the filter size was set to 50 (mm)×100 (mm) and the amount of the photocatalyst 5 (here, titanium oxide) was set to 2.0 g. Thereby, results were obtained as listed below.

TABLE 1

| | THICK-NESS t | AVERAGE CELL NUMBER C | t × C | TOLUENE REMOVAL RATE | EVALUATION |
|---|---|---|---|---|---|
| No. 1 | 10 mm | 9 ppi | 90 | 77.2% | X |
| No. 2 | 15 mm | 9 ppi | 135 | 88.9% | ○ |
| No. 3 | 10 mm | 15 ppi | 150 | 89.7% | ○ |
| No. 4 | 15 mm | 15 ppi | 225 | 92.6% | ○ |
| No. 5 | 15 mm | 25 ppi | 375 | 94.1% | ○ |

To summarize the experimental results, the toluene removal rate was the lowest for the test piece (No. 1) that used the porous metal 11 of 10 t×9 ppi. The toluene removal rate was sufficiently high for the test piece (No. 4) that used the porous metal 11 of 15 t×15 ppi. The toluene removal rate was the highest for the test piece (No. 5) that used the porous metal 11 of 15 t×25 ppi.

Then, the porous metals 11 were evaluated with an 85.0% toluene removal rate as the standard criteria, similar to the case of fine ceramics. The test piece (No. 1) that used the porous metal 11 of 10 t×9 ppi was evaluated as "x (Failed)". The test pieces (No. 2 to No. 5) that used other porous metals 11 were evaluated as "○ (Passed)". The filters using these porous metals 11 were also able to remove acetaldehyde. Specifically, the test pieces (No. 1 to No. 5) that used the porous metal 11 all had the acetaldehyde removal rate of 90.0% or more, hence good results were obtained.

It is considered that the reason for the above results is because increasing the thickness t of the porous metal 11 provided greater contact opportunities of the malodorous components (toluene) with the photocatalyst 5, and thus the toluene removal rate was improved.

It is also considered that the reason for the above results is because increasing the average cell number C of the porous metal 11 provided the increase of the density (crowding) of cells of porous metal 11 and the greater contact opportunities of the malodorous components (toluene) with the photocatalyst 5, and thus the toluene removal rate was improved.

However, if the thickness t of the porous metal 11 increases, the pressure loss increases for the increased thickness. Moreover, if the average cell number C of the porous metal 11 increases, the pressure loss increases for the increased average cell number. Further, the increase in pressure loss reduces the exhaust performance, which makes it difficult to discharge the gas 3 (treated gas 3b) into the atmosphere. Therefore, it is necessary to increase the exhaust capability of the fan. In that case, the situation becomes impractical in terms of exhaust performance.

Accordingly, it is necessary to suppress and lower the pressure loss. To lower the pressure loss, the thickness t of the porous metal 11 may be reduced, or the average cell number C of the porous metal 11 may be reduced (to lower (sparsely spread out) the density of the cells of the porous metal 11). However, because such countermeasures would reduce the contact opportunity between the malodorous components (toluene) and the photocatalyst 5, the toluene removal rate (namely, deodorizing effect) may conversely become reduced.

Specifically, there is a reciprocal relationship between the deodorizing effect and the pressure loss. Therefore, in adopting the porous metal 11 as the new filter substrate 4, it is critical to satisfy both the exhaust performance and the toluene removal rate by optimizing the balance between the deodorizing effect and the pressure loss.

There are commercially available porous metals 11 that have a variety of thicknesses with the average cell number C of 9 ppi, 15 ppi, 25 ppi, or 50 ppi. Moreover, as a result of the examination in which some of the porous metals were used, it has been found that the pressure loss (at 1 m/s) drops when the t×C value is low, and the pressure loss increases when the t×C value is high.

TABLE 2

| | THICK-NESS t | AVERAGE CELL NUMBER C | t × C | TOLUENE REMOVAL RATE | PRES-SURE LOSS | EVALU-ATION |
|---|---|---|---|---|---|---|
| No. 1 | 10 mm | 9 ppi | 90 | 77.2% | 1 Pa | X |
| No. 2 | 15 mm | 9 ppi | 135 | 88.9% | 3 Pa | ○ |
| No. 3 | 10 mm | 15 ppi | 150 | 89.7% | 7 Pa | ○ |
| No. 4 | 15 mm | 15 ppi | 225 | 92.6% | 16 Pa | ○ |
| No. 5 | 15 mm | 25 ppi | 375 | 94.1% | 20 Pa | ○ |
| No. 6 | 10 mm | 50 ppi | 500 | — | 50 Pa | X |

In the case of the test piece (No. 1) that used the porous metal 11 with the t×C value of 90, the pressure loss dropped to 1 Pa. However, in the test piece (No. 1), it was confirmed that the toluene removal rate dropped because the malodorous components (toluene) passed through the filter without obtaining the effective contact state between the malodorous components (toluene) and the photocatalyst 5.

Conversely, in the case of the test piece (No. 6) that used the porous metal 11 with the t×C value of 500, the pressure loss was 50 Pa. Accordingly, it was confirmed that the test piece (No. 6) is not suitable for use because the pressure loss becomes much higher than the pressure loss (20 Pa) of the ceramic filter presently in use. It is preferable for the pressure loss to be suppressed to nearly the same extent as that of the ceramic filter presently in use (approximately 20 Pa) for maintaining and ensuring the exhaust performance equivalent to that of the present situation.

Moreover, amongst the listed test pieces, the test piece (No. 4) using the porous metal 11 of 15 t×15 ppi (t×C=225) was the most suitable for both the exhaust performance and the toluene removal rate. The porous metal 11 of the test piece (No. 4) has the toluene removal rate of 92.6%, the pressure loss of 16 Pa, and the ceramic filter presently in use has the toluene removal rate of 92% to 94% and the pressure loss of approximately 20 Pa. It was confirmed by this examination that the performance nearly equivalent to or better than that of the ceramic filter presently in use is obtained when the porous metal 11 is used in the filter substrate 4. It is thus possible to realize the new photocatalytic filter 6 using the porous metal 11 as the filter substrate 4.

Also in the case of the test piece (No. 5) that used the porous metal 11 with the t×C value of 15 mm×25 ppi=375, the toluene removal rate was 94.1% and the pressure loss was 20 Pa. The pressure loss of the test piece (No. 5) is higher than that of the test piece (No. 4). However, the result of the test piece (No. 5) is within the range of the practical use together with the test piece (No. 4) because the performance thereof was very close to that of the ceramic filter presently in use.

In contrast, in the case of the test piece (No. 6) that used the porous metal 11 of 10 mm×50 ppi=500 was outside the range of the practical use because the pressure loss of 50 Pa was too large.

From the examination results, it was confirmed that the porous metal 11 whose product (t×C) of the thickness t and the average cell number C is from 135 or more to 375 or less is suitable for the filter substrate 4 of the photocatalytic filter 6. Further, it was confirmed that the porous metal 11 with the product in the range from 225 to 375 is more suitable. Although not included in the experimentations and the examinations, there are commercially available porous metals 11 with the t×C value ranging from 225 to 375. It is presumed that the performance nearly equivalent to the test pieces (No. 4) and (No. 5) is obtainable with such commercially available porous metals 11.

Moreover, when the product (t×C) of the thickness t and the average cell number C is lower than 135, the toluene removal rate becomes the same as the reference value, which is 85.0%. Further, when the product (t×C) of the thickness t and the average cell number C is higher than 375, the pressure loss exceeds the value of the ceramic filter presently in use (approximately 20 Pa). Considering the above facts, the product (t×C) that ranges from approximately 100 or more and 400 or less, including margins is allowable. Specifically, if the t×C value is within the range from approximately 100 or more to 400 or less, both the toluene removal rate and the pressure loss are satisfied.

It was ascertained by the examination that when the porous metal 11 whose t×C value is substantially within the range from 100 to 400, the pressure loss and the toluene removal rate become suitable. Specifically, if the porous metal 11, whose t×C value is substantially within the range from 100 to 400, the porous metal 11 can be used as the filter substrate 4 of the photocatalytic filter 6.

In the test piece (No. 6) that used the porous metal 11 with the t×C value of 500, it was clear that the pressure loss was too high and not suitable for practical use, hence the toluene removal rate was not measured.

The porous metal 11 to be newly used as the filter substrate 4 of the photocatalytic filter 6 was studied below.

(2) The porous metal 11 is preferably formed of at least one or more materials selected from a group consisting of nickel (Ni), silver (Ag), copper (Cu), aluminum (Al), nickel-chrome, nickel-tin, and nickel-iron.

Each of Nickel (Ni), silver (Ag), copper (Cu), aluminum (Al), nickel-chrome, nickel-tin, and nickel-iron is preferably pure metal or has a purity of about 99% or more, but alloys thereof may also be used. The porous metal 11 may also be the blend of several types of the above metals in a suitable ratio, or may partially contain the blend.

It is necessary for the porous metal 11 to have a function as the filter substrate 4 of the photocatalytic filter 6, and a function as the support for carrying the photocatalyst 5. It is further preferable that the porous metal 11 itself has a catalytic function.

For the mass-produce of the photocatalytic filter 6 using the porous metal 11 at a lower cost, it is important to select a material of which the porous metal 11 can be stably formed at lower cost and which is suitable for the manufacture and mass production of the porous metal 11.

Therefore, from many metals, materials that satisfy the various requirements were studied. As a result, it was concluded that the porous metal 11 formed of at least one or more materials selected from a group consisting of nickel (Ni), silver (Ag), copper (Cu), aluminum (Al), nickel-chrome, nickel-tin, and nickel-iron or the porous metal 11 containing them is the most suitable. Moreover, by using any of the above materials for the porous metal 11, the photocatalytic filter 6 having good performance can be stably manufactured.

(3) The porous metal 11 preferably contains nickel in the material.

Nickel has a variety of characteristics such as high corrosion resistance, excellent durability, high strength in high and low temperatures, and also has a function as a catalyst. Therefore, by at least partially including nickel in the material for the porous metal 11, the filter substrate 4 becomes highly functional and thus advantageous for obtaining the high-performing photocatalytic filter 6. Moreover, nickel is suitable for the material of the porous metal 11 since it is an excellent metal as described above. Currently, the most widely distributed porous metal 11 contains nickel as the material, and it is the most easily available at a low cost. Accordingly, when using the porous metal 11 in the filter material of photocatalytic filter 6, it is preferable to use one that contains nickel in the material.

(4) The porous metal 11 preferably has a transmittance of 8% or less for an ultraviolet light 8a.

As a result of the examination from another perspective, the photocatalytic filter 6 using the porous metal 11 as the filter substrate 4, it turns out that the t×C value also exerts an influence on ultraviolet light transmittance.

ultraviolet light 8a becomes 8% or less. Specifically, it was confirmed that the porous metal 11 with the transmittance of 8% or less (and 0.0% or more) for the ultraviolet light 8a is suitable as the filter substrate 4 of the photocatalytic filter 6. Moreover, by setting the transmittance of the ultraviolet light 8a to be 8% or less, the photocatalytic filter 6 using the porous metal 11 can be optimized.

If the ultraviolet light transmittance is reduced to 0.0%, the ultraviolet light 8a would not reach the opposite surface of the porous metal 11. As a result, the photocatalyst 5 is not partially activated in the porous metal 11, which may reduce the toluene removal rate. Accordingly, a value barely reaching 0.0% would be the lower limit value of the ultraviolet light transmittance.

(5) The photocatalyst 5 is preferably titanium oxide.

In the ceramic filter presently in use, titanium oxide is used in the photocatalyst 5.

Titanium oxide is a substance (photocatalyst 5) in which the photocatalytic reaction occurs by absorbing only the ultraviolet light 8a without absorbing visible light. Titanium oxide is activated by irradiating the ultraviolet light 8a of the wavelength of 400 nm or less. Titanium oxide decomposes a contamination or dirt (organic matter) adhered to a surface due to the photocatalytic reaction. The effect of titanium oxide as the photocatalyst 5 is generally proportionate to the amount of the light 8 (ultraviolet light 8a) and the area exposed to the light 8. Since titanium oxide is stable and does not change, it has a semi-permanent life as the photocatalyst 5. Since the photocatalyst 5 is hydrophilic, self-

TABLE 3

| | THICKNESS t | AVERAGE CELL NUMBER C | t × C | TOLUENE REMOVAL RATE | PRESSURE LOSS | ULTRAVIOLET LIGHT TRANSMITTANCE | EVALUATION |
|---|---|---|---|---|---|---|---|
| No. 1 | 10 mm | 9 ppi | 90 | 77.20% | 1 Pa | 9.40% | X |
| No. 2 | 15 mm | 9 ppi | 135 | 88.90% | 3 Pa | 4.40% | ○ |
| No. 3 | 10 mm | 15 ppi | 150 | 89.70% | 7 Pa | 1.60% | ○ |
| No. 4 | 15 mm | 15 ppi | 225 | 92.60% | 16 Pa | 0.50% | ○ |
| No. 5 | 15 mm | 25 ppi | 375 | 94.10% | 20 Pa | 0.10% | ○ |
| No. 6 | 10 mm | 50 ppi | 500 | — | 50 Pa | 0.00% | X |

Specifically, it was discovered that when the t×C value decreases, the ultraviolet light transmittance increases, and when the t×C value increases, the ultraviolet light transmittance decreases.

Moreover, it was confirmed that the toluene removal rate was reduced in the case of the test piece (No. 1) that used the porous metal 11 with the t×C value of 90. This is because the ultraviolet light transmittance became too high and the ultraviolet light 8a could not be efficiently used in the porous metal 11 due to the large transmission amount (leakage) of the ultraviolet light 8a from the light source 7.

Conversely, it was confirmed that the toluene removal rate was increased in the case of the test piece (No. 5) that used the porous metal 11 with the t×C value of 375. This is because the ultraviolet light transmittance was reduced and the ultraviolet light 8a could be efficiently used in the porous metal 11 due to the decrease in the transmission amount (leakage) of the ultraviolet light 8a from light source 7.

Accordingly, it was confirmed that the ultraviolet light transmittance may be an indicator for determining whether the photocatalytic filter 6 has optimal performance.

As mentioned above, the t×C value having a range from approximately 100 to 400 is optimal for both the pressure loss and the toluene removal rate. When the t×C value is from approximately 100 to 400, the transmittance of the cleaning and the like can also be performed by using the hydrophilicity of the photocatalyst 5. Accordingly, when using the porous metal 11 in the filter substrate 4, it is considered preferable to use titanium oxide or a substance containing titanium oxide in the photocatalyst 5.

It has been confirmed that titanium oxide as the photocatalyst 5 also has a function of oxidatively degrading polycyclic aromatic hydrocarbons (PAH). The polycyclic aromatic hydrocarbons are generated by incomplete combustion during the heat cooking of food and are contained in cooking gas together with the malodorous components, oil mist (oil smoke), microparticles, and the like. By using titanium oxide in the photocatalyst 5, polycyclic aromatic hydrocarbons together with malodorous components such as toluene and acetaldehyde can be reduced and removed.

According to Formula E, the bandgap of titanium oxide (anatase type) is 3.2 eV, which becomes about 388 nm when converted to wavelength.

Formula E (energy per photon of light 8)=h (Planck constant)×v (frequency of light 8) (where V=speed of light 8÷wavelength; and thus E=h×speed of light 8÷wavelength→E=1240÷wavelength→1240÷387.5 nm=3.2 eV)

Therefore, the adaptive wavelength range of titanium oxide is approximately 380 nm. Accordingly, it is preferable to use an ultraviolet lamp or an ultraviolet LED lamp that emits UV-A (ultraviolet light A of wavelength range 300 to 400 nm) for the light source 7 to activate titanium oxide. Particularly, it is preferable for the ultraviolet lamps or the ultraviolet LED lamps used as the light source 7 to have a peak wavelength range of 380 nm. Moreover, the combination of titanium oxide and the light source 7 with the wavelength range of 380 nm has a function so excellent that it can be used as an air purification apparatus using the photocatalytic reaction.

Titanium oxide may also be used with an additive. Adding the additive makes it possible to produce the photocatalyst 5 having the catalytic effect for the light 8 with wavelengths longer than 400 nm. Furthermore, in addition to titanium oxide, by supporting Pt (platinum), $WO_3$ (tungsten oxide), and other precious metals, as the photocatalyst 5, onto the porous metal 11, the photocatalyst 5 can use the light 8 of the visible light range included in the light source 7. Specifically, the photocatalytic filter 6 that works with the visible light can also be realized.

Accordingly, it was concluded that, for the photocatalytic filter 6 using the porous metal 11 as the filter substrate 4, it is most preferable to use titanium oxide with the excellent properties for the photocatalyst 5.

(6) The photocatalyst 5 preferably has an average particle diameter in a range from 1 nm or more to 100 nm or less.

In the ceramic filter presently in use, nanomaterials (nanoparticles) are used in the material of photocatalyst 5. Nanomaterials are defined by the ISO as follows. "Nanomaterials are solid-state materials produced by using chemical elements etc. as raw material, which are nano-substances and nanostructures configured from nano-substances (including aggregates of nano-substances) wherein at least one dimension of the three dimensions indicating size is about 1 to 100 nm". Moreover, titanium oxide and the like, which is used as the material of the photocatalyst 5, generally falls in the category of nanomaterials because the material such as the titanium oxide of the photocatalyst 5 has an average particle diameter in a range from 1 nm or more to 100 nm.

An attempt was then made to determine whether the photocatalyst 5 with the average particle diameter in a range from 1 nm or more to 100 nm or less could be supported onto the porous metal 11 without hindrance. The method for supporting the photocatalyst 5 onto the porous metal 11 was to, for example, adjust a titanium oxide slurry by adding titanium oxide powders to a peroxotitanic acid solution (PTA solution), impregnate the porous metal 11 by immersing it in this titanium oxide slurry, dry and sinter it.

The titanium oxide slurry may be dispersed by mixing titanium oxide in a dispersing medium such as alcohol, e.g., methanol and ethanol, or water. Surfactants, mineral acids such as hydrochloric acid or sulfuric acid, and carboxylic acids such as acetic acid or citric acid may be added to the dispersing medium as required to promote the dispersion of titanium oxide. Then, the slurry containing titanium oxide particles can be produced by pulverizing and dispersing the titanium oxide particles in the dispersing medium, using equipment such as a bead mill, ball mill, sand mill, roll mill, vibration mill, or a homogenizer.

Furthermore, in addition to titania-based binders such as a peroxotitanic acid solution, silica-based, alumina-based binders, or the like may also be included in the titanium oxide slurry.

Generally used methods such as the dip coating method or spray coating method may be employed as the method for supporting the titanium oxide slurry onto the photocatalyst

5. The method to be used is not limited to the above if the application is suitable for the purpose.

As a result, it was confirmed that the photocatalyst 5 can be supported onto the porous metal 11 only by an amount (support amount), which will be described below. Accordingly, it was concluded that the photocatalyst 5 with the average particle diameter in a range from 1 nm or more to 100 nm or less is suitable for being supported onto the porous metal 11.

(7) The support amount of the photocatalyst 5 onto the filter substrate 4 is preferably in a range from 1 g to 2.5 g per area of 50 mm×100 mm.

In the ceramic filter presently in use, the support amount of the photocatalyst 5 (titanium oxide) is from 1 g to 3 g per area of 50 mm×100 mm. Using this as the reference criteria, the support amount of the photocatalyst 5 (titanium oxide) onto the porous metal 11, which can provide the deodorization performance equivalent to that of the ceramic filter presently in use, was obtained by the experimentation.

The support amount of the photocatalyst 5 was set and adjusted by the amount of the spray of the titanium oxide slurry dispersed in methanol. Subsequently, the experimentation was performed under the conditions in accordance with JIS R 1701-3 for the filter substrate 4 (porous metal 11) supporting the photocatalyst 5. The same porous metals 11 that were used in the test pieces (No 2 to No 5) were used in the experiment.

When the support amount of the photocatalyst 5 (titanium oxide) is low, the toluene removal rate is reduced. When the support amount of the photocatalyst 5 (titanium oxide) is high, it causes clogging of the porous metal 11. Based on the above results, a suitable value range was set so that the toluene removal rate became 85.0% or more and the porous metal 11 was not clogged.

Subsequently, results that slightly differ from those of the ceramic filter presently in use were obtained. Specifically, it was confirmed that the support amount of the photocatalyst 5 onto the porous metal 11 was found to be suitable in a range from 1 g to 2.5 g, resulting in less support amount to be used compared to the ceramic filter.

(8) The porous metal 11 preferably has a flat planar shape.

The ceramic filter presently in use has a flat planar shape. Therefore, it is considered that the photocatalytic filter 6 using the porous metal 11 as the filter substrate 4 may also similarly have the flat planar shape. Moreover, with the photocatalytic filter 6 using the porous metal 11 as the filter substrate 4 having the flat planar shape, the ceramic filter presently in use can be replaced exactly as is with the photocatalytic filter 6 using the porous metal 11 as the filter substrate 4. Subsequently, the flat planar-shaped photocatalytic filter 6 using the porous metal 11 as the substrate is the most advantageous to use. When the ceramic filter presently in use was replaced with the photocatalytic filter 6 using the porous metal 11 as the substrate, good results equivalent to those of the ceramic filter presently in use were obtained. Compared to the ceramic filter, the porous metal 11 has an especially high degree of freedom with respect to the shape. Accordingly, it is possible to adopt shapes other than the flat planar shape. It can be expected that forming the porous metal 11 into shapes other than the flat planar shape would be useful in the development of the new deodorizing apparatus 1.

(9) The deodorizing apparatus 1 is configured with the photocatalytic filter 6.

As shown in FIG. 1, the deodorizing apparatus 1 using this photocatalyst 5 can be provided at the inlet portion, the midway portion, and/or the outlet portion of the exhaust duct 2. The untreated gas 3a enters into the exhaust duct 2 and passes through the deodorizing apparatus 1 provided at the inlet portion, the midway portion, and/or the outlet portion of the exhaust duct 2. Then, the gas 3a is deodorized by the deodorizing apparatus 1 to be the treated gas 3b and the gas 3b flows towards the downstream side to be discharged into the atmosphere. The treated gas 3b discharged into the atmosphere has been deodorized at a high level, and accordingly, there is no concern of causing environmental pollution due to the odor thereof.

The deodorizing apparatus 1 provided at the inlet portion of the exhaust duct 2 is installed, e.g., at a kitchen facility provided in restaurants 22 operating in a commercial establishment 21. In this case, the deodorizing apparatus 1 is disposed, for example, within the inner portion of a range hood 24 installed above a cooking device 23 of the kitchen facility, or a connecting portion between the range hood 24 and the exhaust duct 2 ((small-scale) distributed-type deodorizing apparatus 25). Thereby, the cooking gas from each of the restaurants 22 (installed in the commercial establishment 21) can be individually deodorized. Therefore, the deodorizing apparatus 1 can be made into the smallest size and thus installation space can be minimized, and the management becomes easier because of the individualization of the deodorizing apparatus 1. Furthermore, the contamination or dirt in the entire exhaust duct 2 is also reduced.

Further, the deodorizing apparatus 1 provided at the midway portion of the exhaust duct 2 is provided, e.g., at the branch duct 2a installed on each floor of the commercial establishment 21 (medium-scale distributed-type deodorizing apparatus 26). The medium-scale distributed-type deodorizing apparatus 26 is installed, e.g., at one or several locations such as at the mid-way of the branch duct 2a or an upstream side of the fire damper 27 located near the outlet portion of the branch duct 2a. Thereby, the cooking gas from each of the restaurants 22 (installed at the commercial establishment 21) can be collectively deodorized on each floor. Therefore, the deodorizing apparatus 1 can be made into a medium-scale and thus installation space can be smaller, and the management becomes easier because it is necessary to do so only on each floor. Furthermore, the contamination or dirt in the entire exhaust duct 2 can also be suppressed.

Moreover, the deodorizing apparatus 1 provided at the outlet portion of the exhaust duct 2 is installed collectively as one unit at, e.g., the rooftop 21a of the commercial establishment 21 (centralized-type deodorizing apparatus 28). The centralized-type deodorizing apparatus 28 is provided at the collective duct 2b, which joins the branch ducts 2a on each floor and extends to the rooftop 21a. Thereby, the cooking gas from each of the restaurants 22 can be collected at one place and deodorized once. Moreover, the deodorizing apparatus 1 can be made into a large size to be able to perform one-batch management (or centralized management). Therefore, the management of the deodorizing apparatus 1 at each restaurant 22 and each floor becomes unnecessary. Moreover, the treated gas 3b can be easily discharged into the atmosphere because of the high location of the rooftop 21a. If the exhaust duct 2 has several systems, the centralized-type deodorizing apparatus 28 may be provided at each of the systems of the exhaust duct 2.

In the deodorizing apparatus 1, any one of the distributed-type deodorizing apparatus 25, the medium-scale distributed-type deodorizing apparatus 26, and the centralized-type deodorizing apparatus 28 may be provided, or at least one or more, or all of these deodorizing apparatuses 25, 26, and 28 may be provided at the exhaust duct 2.

More specifically, the distributed-type deodorizing apparatus 25 is configured and provided as shown in FIGS. 3 to 7 (see mainly FIG. 4), for example.

The distributed-type deodorizing apparatus 25 may be provided in an integrated manner, e.g., in the range hood 24 connected to the exhaust duct 2 (branch duct 2a). The distributed-type deodorizing apparatus 25 may be detachably installed to the range hood 24 with the main body portion made into one unit (deodorizing unit 31). The deodorizing unit 31 is installed at a location, e.g., the downstream side (upper side) of a fan 32 installed inside the range hood 24.

The distributed-type deodorizing apparatus 25 is powerful enough to be able to deodorize the malodorous components in the gas 3 to a level that humans can hardly perceive. Therefore, it is structurally possible to discharge the gas 3 (treated gas 3b), which has passed through the distributed-type deodorizing apparatus 25, back to inside the building instead of discharging it through the exhaust duct 2 outside.

The deodorizing unit 31 is integrated by installing, for example, the photocatalytic filter 6 and light source 7 in the rack 33 in the order from the upstream side (lower side) to the downstream side (upper side).

The rack 33 is a member constituting the external portion of the deodorizing unit 31. The photocatalytic filter 6 and the light source 7 may be provided having a single stage or multiple stages in an alternating manner along the flow direction of the gas 3 (up-down direction) within the rack 33. In the present embodiment, the photocatalytic filters 6 are provided parallel to each other having three or stages in an up-down direction, and the light sources 7 are provided having the two or more stages in a space between the photocatalytic filters 6 in the up-down direction. One or more of the light sources 7 is provided in each space. The light source 7 may be the ultraviolet lamp or ultraviolet LED lamp. The light source 7 is preferably arranged with only the necessary number of the lamps so that the light 8 spreads out substantially equally throughout the entire surface of the photocatalytic filter 6. The light source 7 may be provided at the downstream side (upper side) of the last stage (uppermost stage) of the photocatalytic filter 6. However, such light source 7 is not particularly necessary and thus may be omitted.

Moreover, a grease filter 34 is preferably mounted on the surface of the upstream side (bottom surface) of the first stage of the photocatalytic filter 6 in the rack 33. The grease filter 34 may be a filter having a wire-mesh to which oil mist adheres and from which the mist is then removed. An auxiliary filter such as an activated charcoal filter 35 may also be additionally mounted as required on the surface of the downstream side (top surface) of the last stage of the photocatalytic filter 6 in the rack 33.

The rack 33 is a storage part which the grease filter 34, the photocatalytic filter 6, the light source 7, and the auxiliary filter such as the activated charcoal filter 35 can be individually attached to and detached from. The storage part includes a shelf therewithin, for example. The grease filter 34, the photocatalytic filter 6, and the activated charcoal filter 35 are installed (laterally) onto the shelf portion of the storage part such as to traverse the flow path cross-section of the gas 3 inside the range hood 24. The grease filter 34, the photocatalytic filter 6, and the activated charcoal filter 35 are closed the flow path of the gas 3 in the range hood 24 and divide the flow path into the upstream side and the downstream side, respectively.

The rack 33 itself is also formed into a shape and size such as to close the flow path cross-section of the gas 3 in the range hood 24, and installed within the range hood 24 to be attached thereto and detached therefrom.

Figure 5:
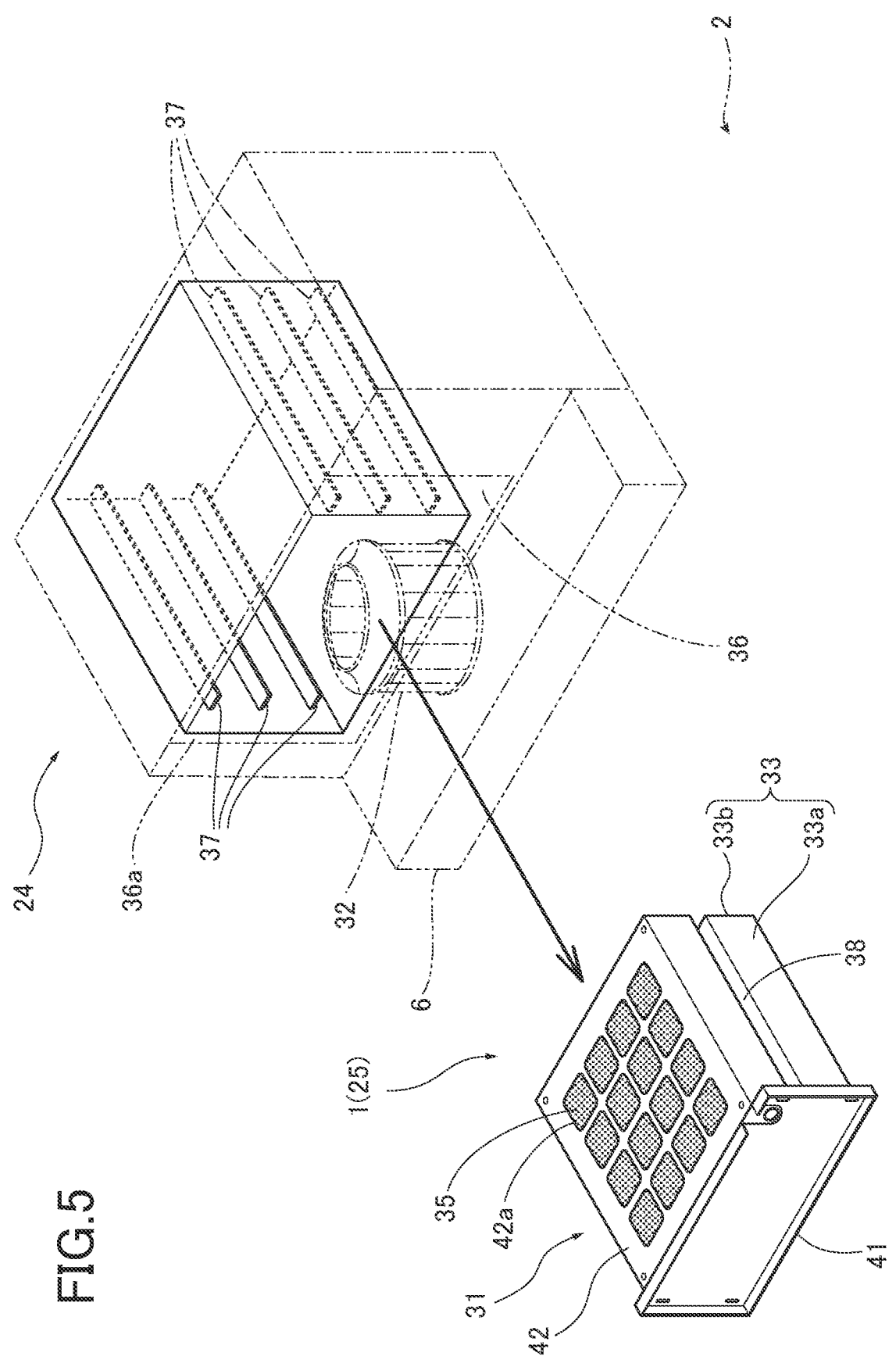
FIG. 5 is a perspective view illustrating a state in which the deodorizing unit of FIG. 4 is attached to and detached from the range hood.

As shown in FIG. 5, the attaching and detaching direction of the rack 33 relative to the range hood 24 or the exhaust duct 2 is preferably in a substantially horizontal direction (front-back direction) joining the front side and the back side, in a state of facing straight into the range hood 24.

Inside the range hood 24, a mounting portion 36 is provided for the rack 33. The mounting portion 36 is a space that forms the flow path of the gas 3 communicating between the fan 32 and the exhaust duct 2 (branch duct 2a).

The front side of the mounting portion 36 is configured as the opening portion 36a, and the rack 33 is attached by being laterally inserted to the opening portion 36a from the front side to the back side. Guide members 37 (sliding guides) are provided on both side surfaces inside the mounting portion 36. The guide members 37 extend in the attaching and detaching direction of the rack 33 to guide the attachment and detachment of the rack 33.

The guide members 37 are at least provided at locations corresponding to the bottom surface of the rack 33 to support the bottom surface of the rack 33 from the bottom. The guide members 37 may be provided at locations corresponding to the top surface of the rack 33 to support the top surface of the rack 33 from the top. The guide members 37 may also be provided at locations corresponding to the midway portions of the side portions 33a of the rack 33 to guide the guide recesses 38 provided at the midway portions of the side portions 33a of the rack 33.

Figure 6:
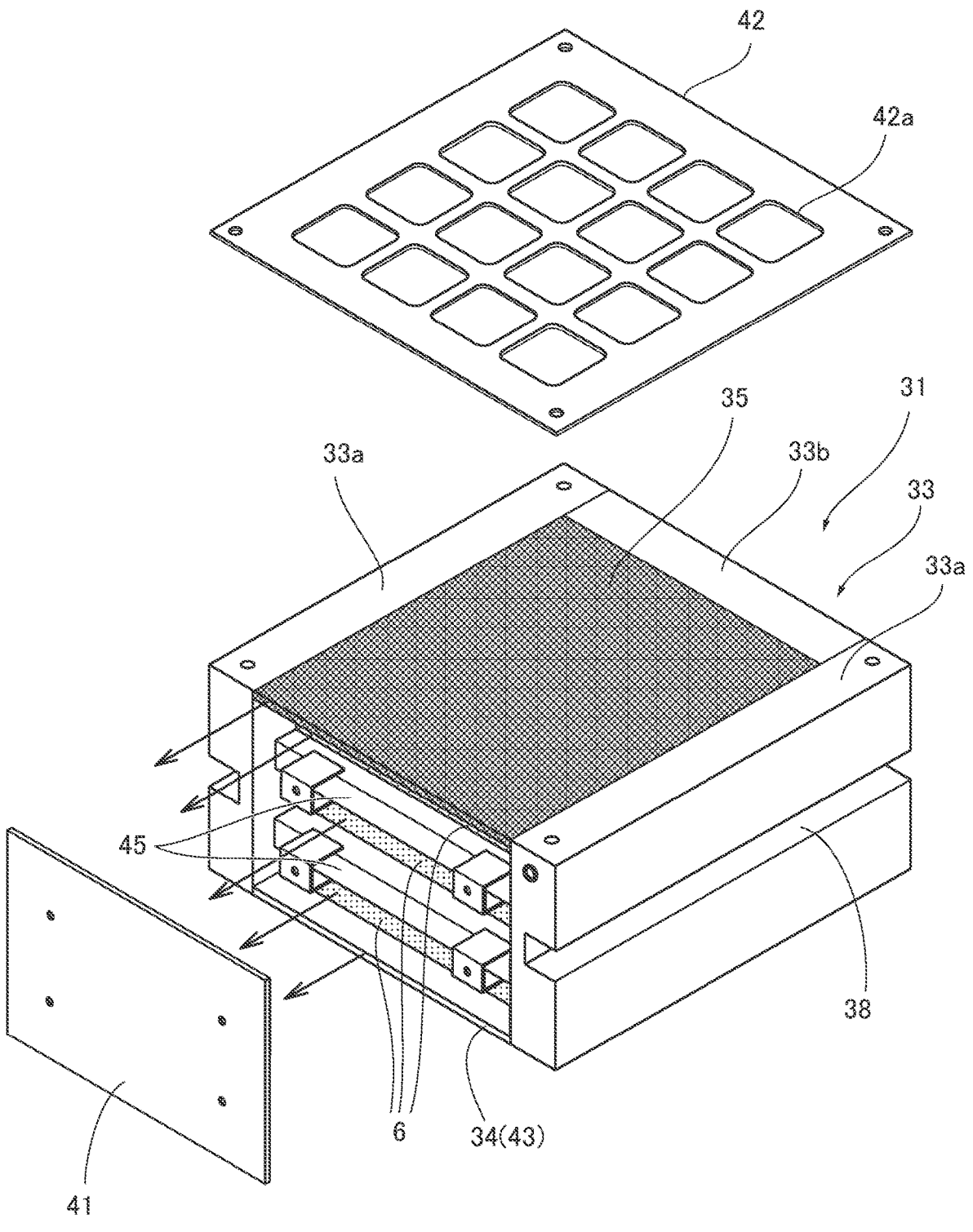
FIG. 6 is an exploded perspective view of the deodorizing unit of FIG. 5.

As shown in FIG. 6, the rack 33 is a frame member having a substantially C shape when seen from the top. The rack 33 includes left and right side portions 33a, and a back portion 33b, and the front, top, and bottom sides of the rack 33 are open.

A front side member 41, a top side member 42, and a bottom side member 43 are detachably attached to the front, top, and bottom sides of the rack 33, respectively. The front side member 41, the top side member 42, and the bottom side member 43 are removably fixed to the rack 33 with screws, for example.

Figure 7:
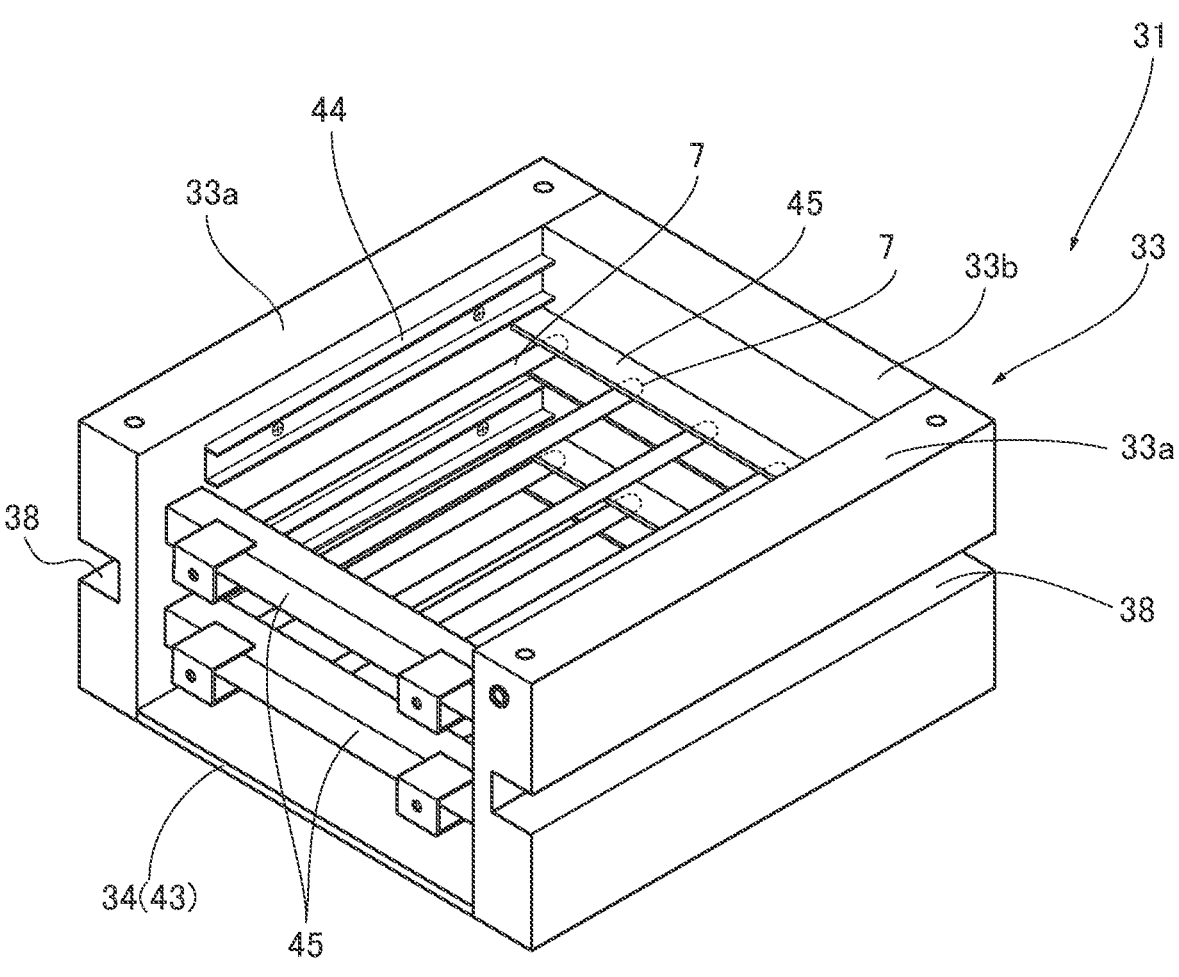
FIG. 7 is a perspective view of the rack of the deodorizing unit of FIG. 6.

The photocatalytic filter 6, the light source 7, and the activated charcoal filter 35 are exposed by removing at least the front side member 41 and the top side member 42 from the rack 33, and thus the photocatalytic filter 6, the light source 7, and the activated charcoal filter 35 can be attached to or detached from the rack 33. As shown in FIG. 7, detachable shelf portions 44 (sliding guides) are provided in the up-down direction within the rack 33 in accordance with the number of the photocatalytic filters 6 (number of installation stages) and arranged spaced apart from each other to leave a space therebetween. The shelf portions 44 are configured so that the photocatalytic filters 6 are laterally inserted from the front side to the back side. Moreover, light source sockets and light source holders 45 that hold the light sources 7 and supply power to the light sources 7 are provided in accordance with the number of the installation stages of the light source 7, in the up-down direction spaced apart from each other.

Moreover, as shown in FIG. 5, the front side member 41 may be formed to have a flange surface larger than the opening portion 36a of the mounting portion 36 so that the rack 33 may close the opening portion 36a of the mounting portion 36 by the flange surface of the front side member 41.

As shown in FIG. 6, the top side member 42 may also be formed as a perforated plate having a plurality of through-holes 42a and provide to retain the activated charcoal filter 35 from the top with the perforated plate. The bottom side member 43 may consist of the grease filter 34 and the grease filter 34 may directly close the bottom surface of the rack 33.

Then, the deodorizing unit 31 is installed to the mounting portion 36 of the exhaust duct 2, and accordingly, the deodorizing unit 31 closes the entire flow path cross-section of the gas 3 within the range hood 24. Thereby, the entire amount of the gas 3 passes through the rack 33 of the deodorizing unit 31. Accordingly, the gas 3 is deodorized by the photocatalytic reaction of the photocatalytic filter 6 and the like provided within the rack 33.

Configuring the distributed-type deodorizing apparatus 25 as described above, the entire deodorizing unit 31 of the distributed-type deodorizing apparatus 25 can be removed all at once with the rack 33 from the mounting portion 36 of the range hood 24, which is provided at a higher position near the ceiling. In the removed deodorizing unit 31, the photocatalytic filter 6, the light source 7, and the activated charcoal filter 35 installed in the rack 33 can be exposed by removing the front side member 41 and the top side member 42 of the rack 33 at a lower position. Accordingly, the grease filter 34 on the bottom surface, the photocatalytic filter 6, the light source 7, and the activated charcoal filter 35 can be removed from the deodorizing unit 31 as required and thus the removed members can be easily maintained.

After the maintenance is finished, the grease filter 34, the photocatalytic filter 6, the light source 7, and the activated charcoal filter 35 are mounted in the rack 33 back to their original positions, and then, the front side member 41 and the top side member 42 are attached to the rack 33. Then, the deodorizing unit 31, of which the maintenance was finished, can then be mounted all at once with the rack 33 in the mounting portion 36 of the exhaust duct 2, which is located at the higher position. This reduces the work at the higher position and makes the maintenance easier.

Figure 8:
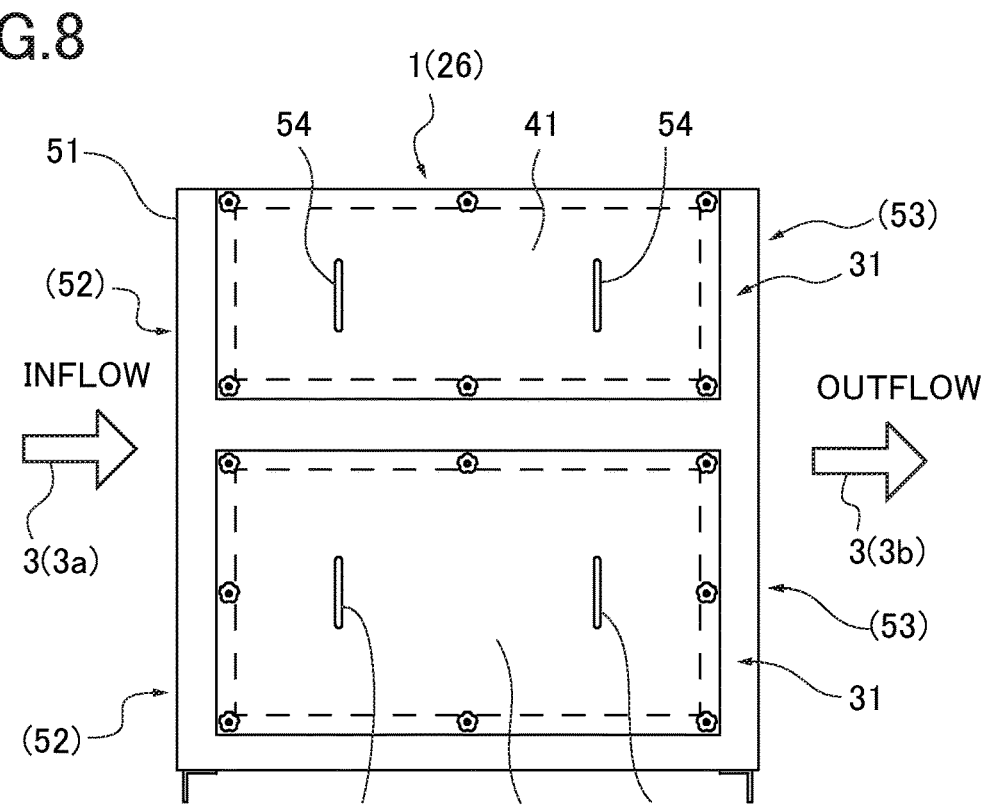
FIG. 8 is a general side view of a medium-scale distributed-type deodorizing apparatus.
Figure 9:
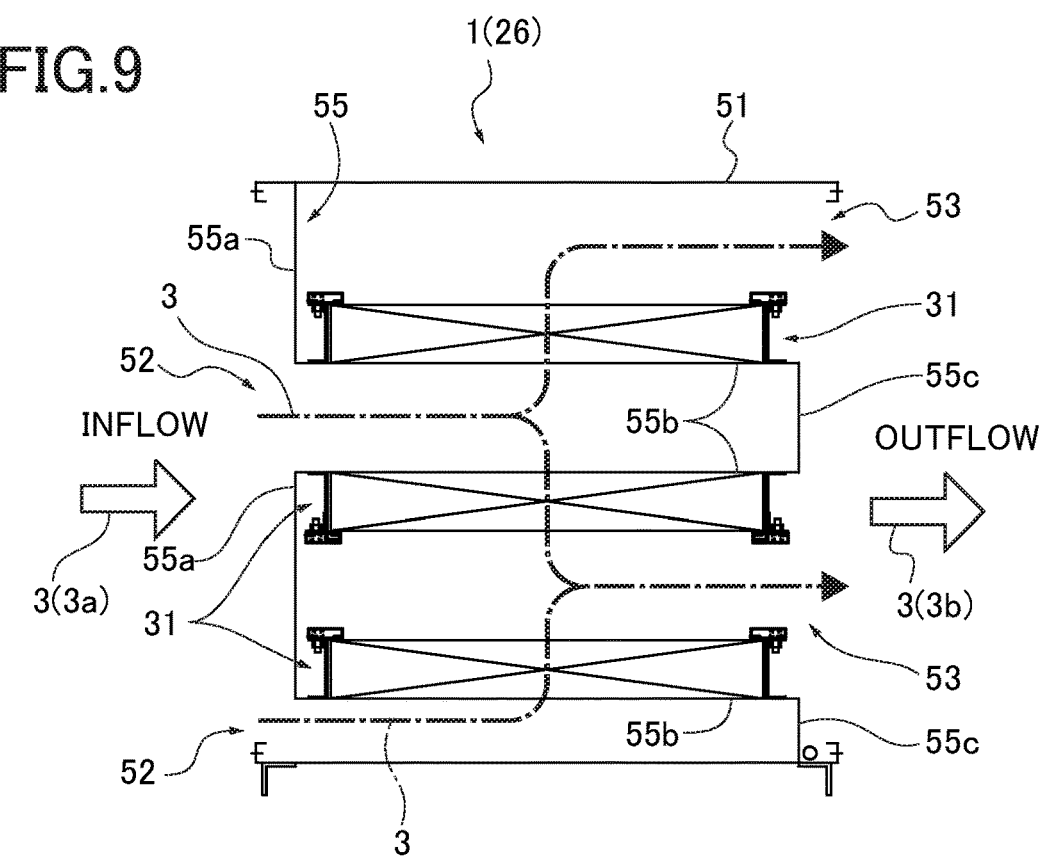
FIG. 9 is a longitudinal cross-sectional view of the medium-scale distributed-type deodorizing apparatus of FIG. 8.

The medium-scale distributed-type deodorizing apparatus 26 is shown in FIGS. 8 and 9, for example.

The medium-scale distributed-type deodorizing apparatus 26 includes a hollow, box-shaped casing 51, which is placed in the mid-way of the exhaust duct 2 (branch duct 2a). The deodorizing unit 31 similar to the one described above is attached to and detached from the casing 51 between the front side and the back side of the casing 51.

The attaching and detaching direction of the deodorizing unit 31 relative to the casing 51 is in a substantially horizontal direction intersecting the flow direction of the gas 3 flowing through the exhaust duct 2. An opening for attaching and detaching the deodorizing unit 31 is provided at the front side of the casing 51, which is the front side of the attaching and detaching direction.

The casing 51 includes flow inlet portions 52 and flow outlet portions 53 for the gas 3. The flow inlet portions 52 are provided at the surface located at the upstream side of the flow direction of the gas 3 flowing through the exhaust duct 2. The flow outlet portions 53 are provided at the surface located at the downstream side. The casing 51 is mounted in the commercial establishment 21 onto the ceiling or the wall surface where the exhaust duct 2 (branch duct 2a) is provided. The deodorizing unit 31 may be configured substantially similarly to that of the distributed-type deodorizing apparatus 25. A handle 54 for attaching to and detaching from the casing 51 may be provided on the front surface which is located in the front side of the attaching and detaching direction of the deodorizing unit 31.

If the flow direction of the gas 3 in the exhaust duct 2 is substantially horizontal, the photocatalytic filter 6 may also be installed in an orientation perpendicular to the flow direction of the gas 3 (vertical placement). However, in the present embodiment, the photocatalytic filter 6 is installed in an orientation parallel to the flow direction of the gas 3 (horizontal placement).

Therefore, the casing 51 includes a dividing wall 55 that divides the interior of the casing 51 into an upstream section and a downstream section. The dividing wall 55 is installed to extend from the bottom surface to the top surface of the casing 51. Moreover, the dividing wall 55 is formed into a zig-zag folding shape when seen from the side thereof by alternatingly arranging one or more of vertical sections 55a, 55c, and one or more of horizontal sections 55b. The horizontal section 55b of the dividing wall 55 is formed as a shelf and the deodorizing unit 31 is laterally placed onto the horizontal section 55b.

The horizontal section 55b formed as a shelf includes through holes. Thereby, the gas 3 passes from the upstream section to the downstream section of the casing 51 and through the deodorizing unit 31 on the shelf via the through-holes.

The vertical sections 55a of the dividing wall 55 are located at the upstream side in the casing 51, and the vertical sections 55c of the dividing wall 55 are located at the downstream side in the casing 51. The vertical sections 55a at the upstream side and the vertical sections 55c at the downstream side are provided at different heights. The horizontal sections 55b substantially horizontally connect the vertical sections 55a at the upstream side and the vertical sections 55c at the downstream side. Thereby, the dividing wall 55 entirely extends in the up-down direction and has a serpentine (meandering) shape where the wall turns once or more times in the horizontal direction along the flow direction of the gas 3. For example, the dividing wall 55 may be formed into the serpentine shape by connecting a plurality of metal plates or may be formed into the serpentine shape by bending one metal plate (or a plurality of metal plates).

The flow inlet portions 52 of the casing 51 are formed at the upstream side of the casing 51 at a location where the vertical sections 55a at the upstream side do not exist. The flow outlet portions 53 of the casing 51 are formed at the downstream side of the casing 51 at a location where the vertical sections 55c at the downstream side do not exist. The flow inlet portions 52 and the flow outlet portions 53 are provided at locations with differing heights in the up-down direction.

In the present embodiment, by having the two vertical sections 55a, the two vertical sections 55c, and the three horizontal sections 55b constituting the dividing wall 55, the flow outlet portions 53 and the flow outlet portions 53 are formed at two locations in the up and down direction, respectively, and deodorizing units 31 are provided at three stages in the up-down direction. The deodorizing units 31 may be independently provided in the up and down direction or may be integrated by connecting them to the front side member 41. In the present embodiment, the one upper side deodorizing unit 31 is in an independent state, and the two lower side deodorizing units 31 are in a state connected by the common front side member 41 in the up and down direction. However, the configuration of the medium-scale distributed-type deodorizing apparatus 26 is not limited to the above configuration.

By configuring as described above, the medium-scale distributed-type deodorizing apparatus 26 can obtain advantages similar to that of the distributed-type deodorizing apparatus 25. Further, by installing the photocatalytic filter 6 parallel to the flow direction of the gas 3 in the medium-scale distributed-type deodorizing apparatus 26, the photocatalytic filter 6 can be freely formed to any size without being limited by the flow path cross-section of the exhaust duct 2 and the medium-scale distributed-type deodorizing apparatus 26 can be easily installed to the exhaust duct 2.

Figure 10A:
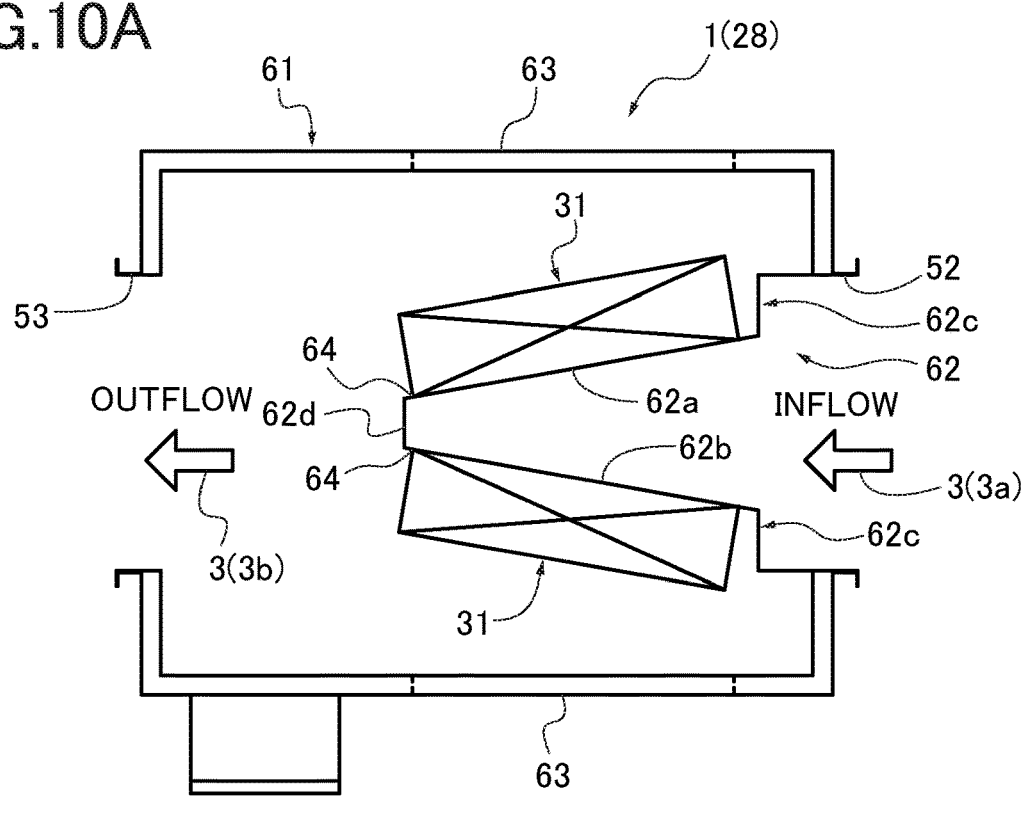
FIG. 10A is a cross-sectional view of a centralized-type deodorizing apparatus.
Figure 10B:
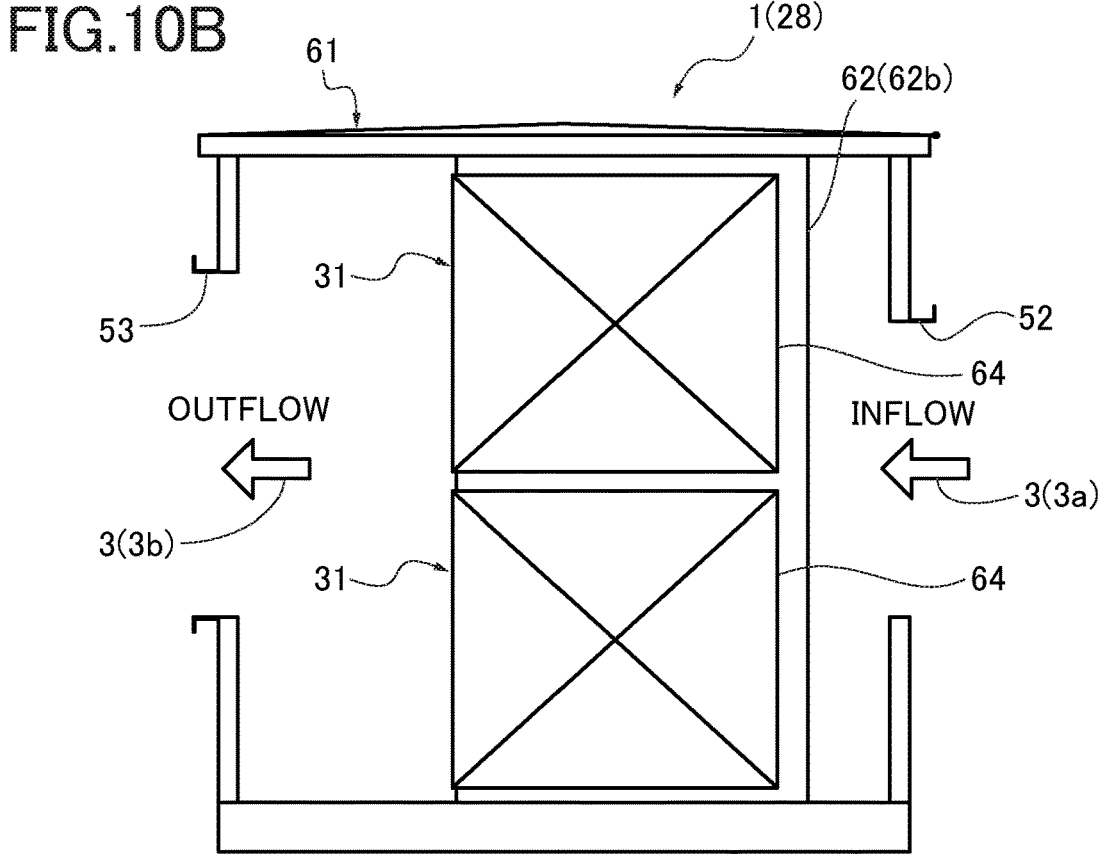
FIG. 10B is a longitudinal cross-sectional view of a centralized-type deodorizing apparatus.

Moreover, as shown in FIGS. 10A and 10B, the centralized-type deodorizing apparatus 28 is installed in a large-sized, hollow housing 61 (building) mounted at the outlet portion of the exhaust duct 2 (collective duct 2b). The centralized-type deodorizing apparatus 28 includes a partition wall 62 that divides the housing 61 into an upstream side space and a downstream side space. A plurality of deodorizing units 31 is provided to be fitted on the surface of the partition wall 62.

The housing 61 has a substantially rectangular parallelepiped shape, for example. The housing 61 includes a flow inlet portion 52 at one end of the housing 61 to which the exhaust duct 2 is connected, and a flow outlet portion 53 at the other end (the other surface). However, the shape of the housing 61 is not limited to the above shape.

It is preferable to provide the partition wall 62 to be substantially located between the side sections of the flow inlet portion 52 and surround portions in the periphery of the flow inlet portion 52. The partition wall 62 is formed to have a height extending from the floor surface to the ceiling of the housing 61.

Moreover, the partition wall 62 is preferably provided to have a substantially V-shape in a plan view, so that the portions of the partition wall 62 surrounding the periphery portions of the flow inlet portion 52 taper from the flow inlet portion 52 to the flow outlet portion 53. The partition wall 62 includes at least two diagonal wall sections 62a and 62b that constitute the substantially V-shape in a plan view.

The interval or gap between the end sections of the two diagonal wall sections 62a and 62b at the flow inlet portion 52 side is set to be substantially the same as the width of the flow inlet portion 52 or narrower than the width of the flow inlet portion 52. If the interval between the end sections is not equal to the width of the flow inlet portion 52 (e.g., narrower), step walls 62c may be provided between the side sections of the flow inlet portion 52 and the end sections of the two wall sections 62a and 62b at the flow inlet portion 52 side. The step walls 62c are provided to adjust the width difference therebetween. The interval between the flow inlet portion 52 and the two wall sections 62a and 62b may be connected by the step walls 62c.

The end sections of the two diagonal wall sections 62a and 62b at the flow outlet portion 53 side may be directly connected to each other, but may also be connected via a short connecting wall 62d.

The partition wall 62, which has the substantially V-shape in a plan view, may have a length half or more of a length from the flow inlet portion 52 to the flow outlet portion 53 of the housing 61. Moreover, the partition wall 62, which has the substantially V-shape in a plan view, may have a length equal to or less than the length from the flow inlet portion 52 to the flow outlet portion 53 of the housing 61.

In the present embodiment, the length of the partition wall 62 is of a length substantially two-thirds (⅔) of the length from the flow inlet portion 52 to the flow outlet portion 53 of the housing 61.

By configuring as described above, the centralized-type deodorizing apparatus 28 can obtain advantages similar to the distributed-type deodorizing apparatus 25 and the medium-scale distributed-type deodorizing apparatus 26. Further, in the centralized-type deodorizing apparatus 28, by configuring the partition wall 62 to have the substantially V-shape in a plan view, the partition wall 62 can be made more compact, and the number of the deodorizing units 31 attached to the partition wall 62 can be reduced.

Moreover, the inside of the housing 61 is partitioned and divided by the partition wall 62, which has the substantially V-shape in a plan view, with an asymmetrical proportion, so that the space at the upstream side is relatively narrower (smaller volume), and the space at the downstream side is relatively wider (larger volume). Further, the partition wall 62, which has the substantially V-shape in a plan view, makes the space at the upstream side gradually smaller as the flow path cross-section proceeds towards the flow outlet portion 53.

Subsequently, the untreated gas 3*a* entering into the housing 61 from the flow inlet portion 52 moves straight forward and directly hits the partition wall 62, which has the substantially V-shape in a plan view. The untreated gas 3*a* then moves towards the flow outlet portion 53 and the pressure of the untreated gas 3*a* becomes higher as the flow path cross-section gradually becomes smaller due to the substantially V-shaped partition wall 62. The differential pressure between the higher pressure of the upstream narrower space and the lower pressure of the downstream wider space forces the untreated gas 3*a* to pass through the partition wall 62. Accordingly, the untreated gas 3*a* is efficiently deodorized by the deodorizing units 31 provided at the partition wall 62. The treated gas 3*b* deodorized by the deodorizing units 31 passes through the flow outlet portion 53 from the space at the downstream side and is discharged to the atmosphere.

In the present embodiment, the partition wall 62 has the substantially V-shape in a plan view. However, the shape of the partition wall 62 is not limited to the above shape.

Moreover, the housing 61 includes one or more inspection doors 63 at one or both of the side surfaces of the housing 61. Each of the inspection doors 63 is openable and closeable to enter or exit the space at the downstream side during the inspection. Each of the inspection doors 63 preferably opens outward.

Moreover, the partition wall 62 includes a plurality of mating or fitting openings 64 that enable the attachment and detachment of the deodorizing units 31. Each of the fitting openings 64 is formed to have substantially the same size and shape as the external shape of the deodorizing unit 31 so that the deodorizing unit 31 is fitted into the fitting opening 64 and fixed thereto. Each of the deodorizing units 31 is detachably mounted into the fitting opening 64 in a vertically orientated state.

The deodorizing unit 31 may be attached to and detached from the fitting opening 64 from the space at the upstream side or the space at the downstream side. However, it is preferable for the deodorizing unit 31 to be attached and detached from the side where the inspection door 63 is provided (space at the downstream side in the present embodiment) from the maintenance perspective.

Preferably, the fitting openings 64 may be formed on the partition wall 62 regularly arranged, for example, in the up-down direction or the left-right direction, or may be formed as a grid pattern arranged in up-down and left-right directions.

Figure 11:
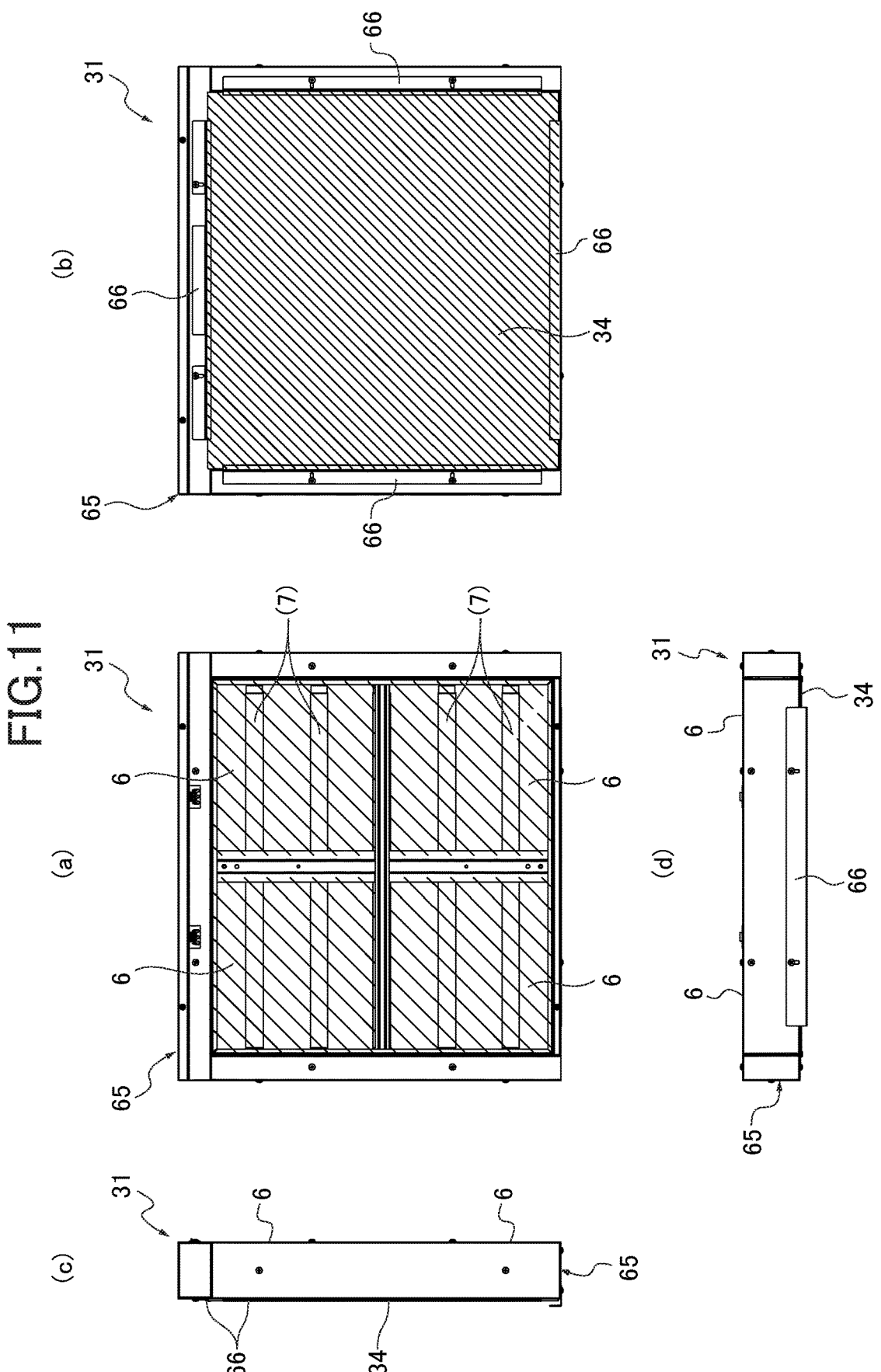
FIG. 11 illustrates the deodorizing unit of FIG. 10A, where (a) is a rear view, (b) is a front view, (c) is a side view, and (d) is a bottom view.

As shown in FIG. 11, the deodorizing unit 31 for the centralized-type deodorizing apparatus 28 has a configuration and function substantially similar to those of the distributed-type deodorizing apparatus 25 and the medium-scale distributed-type deodorizing apparatus 26. This deodorizing unit 31 is integrated by alternately installing the photocatalytic filter 6 and the light source 7 in the order from the upstream side. The deodorizing unit 31 may be integrated by inserting the light source 7 between a pair of (two) photocatalytic filters 6 each having a flat planar shape, for example. The deodorizing unit 31 may also be integrated by respectively inserting the light sources 7 between two or more spaces formed between three or more of the photocatalytic filters 6, each having a flat planar shape.

The deodorizing unit 31 includes a frame portion 65 that is the main body. The photocatalytic filter 6 and the light source 7 are detachably mounted onto the frame portion 65. Two or three or more of the photocatalytic filters 6 are arranged parallel to the frame portion 65 along the thickness direction of the frame portion 65 (flow direction of gas 3) in a plurality of stages. In the surface direction of the frame portion 65, a single or plurality of photocatalytic filters 6 are arranged and located within the same surface at each stage to close the entire cross-section of the frame portion 65. The frame portion 65 has a function similar to that of the rack 33 shown in FIGS. 6 and 7. In this case, the frame portion 65 is formed into a rectangular shape.

The frame portion 65 may be formed into the same size as that of one photocatalytic filter 6. Alternatively, the frame portion 65 may be formed larger than the photocatalytic filter 6 such as to arrange the photocatalytic filters 6 in the up-down and left-right directions relative to the same surface to close the entire surface of the frame portion 65. In the present embodiment, the frame portion 65 has a size to be substantially an integer multiple larger than the size of a side of the photocatalytic filter 6. For example, the size of the frame portion 65 is equal to the size of the total of the four photocatalytic filters 6 which are arranged such that two of them are vertically installed and the other two of them are horizontally installed. Moreover, by replacing the filter substrate 4 with the porous metal 11, the photocatalytic filter 6 can have a larger size than that of the existing filter substrate. Accordingly, the one large-sized photocatalytic filter 6 may be installed in the same surface of the frame portion 65 instead of arranging, within the same surface of the larger frame portion 65, the plurality of smaller photocatalytic filters 6 (four photocatalytic filters arranged vertically and horizontally) having the same size as the existing filter. Thereby, the entire surface of the frame portion 65 is closed by one photocatalytic filter 6.

A plurality of light sources 7 is provided in the frame portion 65 to be separated from each other in the up-down direction. In the present embodiment, four light sources 7 are disposed parallel to each other in the frame portion 65. Among them, the two upper side light sources 7 are laterally installed relative to two upper side photocatalytic filters 6 laterally arranged to straddle between the two photocatalytic filters 6. Further, the two lower side light sources 7 are laterally installed relative to two lower side photocatalytic filters 6 laterally arranged to straddle between the two photocatalytic filters 6. The light source 7 may also be vertically installed.

Moreover, the frame portion 65 may be provided with a grease filter 34 to the upstream side surface such that the grease filter is attachable and detachable via a pressing member 66. The grease filter 34 provided to the frame portion 65 is preferably one filter having a size and shape covering the entire surface of the frame portion 65. A single or plurality of pressing members 66 are preferably provided so that each side of the grease filter 34 is pressed relative to each side of the frame portion 65. The pressing members 66 may be sliding guides (or slide rails) and the like to guide the attachment and detachment of the grease filter 34 along the surfaces of the frame portion 65. The respective sliding guides extend along the respective sides of the frame portion 65. Accordingly, when one of the sliding guides along one of the sides is removed, the grease filter 34 can be attached to or detached from the section of the removed side by sliding the grease filter in the direction orthogonal to the removed side.

The grease filter 34 may be individually provided in each of the deodorizing units 31. In addition to the above or alternatively, the grease filter 34 may be collectively provided having a size to close the entire surface of the flow inlet portion 52 at a location upstream of the partition wall 62 of the housing 61, for example, at the inlet section of the flow inlet portion 52.

(Operational Advantages) According to the present embodiment, the following operational advantages may be obtained.

For example, as shown in FIG. 1, the large-scale commercial establishment 21 such as a large-scale shopping mall (large-scale commercial establishment) has many restaurants 22. Generally, each of the restaurants 22 is independently provided with the kitchen facility (cooking device 23).

Many of such kitchen facilities are used for cooking with heat. Then, when cooking with heat, a large amount of the gas 3 (cooking gas) is inevitably emitted. A large amount of the gas contains oil smoke (oil mist) and cooking odors. Subsequently, if such gas is discharged into the atmosphere as it is, there is a concern of generating environmental pollution due to the odors and the like. Accordingly, it is necessary to remove the oil smoke and the cooking odors from the cooking gas before discharging them into the atmosphere.

Therefore, the deodorizing apparatus 1 is installed at the exhaust duct 2 or the like which leads the cooking gas from each kitchen facility outside. The deodorizing apparatus 1 that is used in the large-scale commercial establishment is required to be very powerful to deodorize a large amount of the cooking gas at a high level. Accordingly, the low-level deodorizing apparatuses 1 with no sufficient deodorizing ability cannot be used at the large-scale commercial establishment, and accordingly, it differs from the objective of the deodorizing apparatus 1 according to the present embodiment.

Moreover, there is a variety of deodorizing apparatuses 1 which are employed at the large-scale commercial establishments, such as an absorption-typed deodorizing apparatus using activated charcoal or the like, a neutralizing-typed deodorizing apparatus using a neutralizer, and a bio-typed deodorizing apparatus using micro-organisms. The above technologies have merits and drawbacks, and currently, the various deodorizing apparatuses are used with one another.

In addition to the above deodorizing apparatuses, the deodorizing apparatus 1 using the photocatalyst 5 and the like has also been developed and has been already in practical use. The deodorizing apparatus 1 using the photocatalyst 5 has a higher capability to remove the malodorous components (deodorizing efficiency) compared to other types of the deodorizing apparatuses 1, and thus can effectively remove the cooking odors from the large amount of the cooking gas emitted at the large-scale commercial establishments. Therefore, the deodorizing apparatus 1 using the photocatalyst 5 has an advantage compared to other types of the deodorizing apparatuses 1.

Moreover, the deodorizing apparatus 1 using the photocatalyst 5 can be easily simplified and compact compared to other types of the deodorizing apparatuses 1. Moreover, the photocatalyst 5 exhibits a self-renewing function using the light 8 as an energy source. Subsequently, in the deodorizing apparatus 1 using the photocatalyst 5, there is no need for the waste treatment of the photocatalytic filter 6 and the photocatalytic filter 6 can be used semi-permanently, which reduces the running cost.

In addition to the large-scale commercial establishments, the deodorizing apparatus 1 using such a photocatalyst 5 can also be widely used at ventilated facilities such as ordinary-scale commercial establishments 21, office buildings, or housing complexes such as high-rise condominiums.

The deodorizing apparatus 1 using the photocatalyst 5 includes at least the photocatalytic filter 6 in which the photocatalyst 5 is supported on the filter substrate 4, and the light source 7 that activates the photocatalyst 5. In the deodorizing apparatus 1 using the photocatalyst 5, the light source 7 is illuminated, the photocatalyst 5 is activated by the light 8 from the light source 7, and the gas 3 (untreated gas 3a) such as the cooking gas passes through the photocatalytic filter 6. Thereby, the deodorizing apparatus 1 using the photocatalyst 5 collects the malodorous components of the cooking odors in the cooking gas by the photocatalytic filter 6 and decomposes the collected malodorous components by the photocatalyst 5.

The light source 7 emits the light 8 (primarily ultraviolet light 8a) that activates the photocatalyst 5, and the fluorescent lamp (ultraviolet lamp), LED (ultraviolet LED lamp) and the like may be used. The light source 7 is installed at the downstream side of the photocatalytic filter 6. Thereby, the light source 7 is protected from the untreated gas 3a by the photocatalytic filter 6.

The light 8 from the light source 7 is directly irradiated onto one of the surfaces (downstream surface) of the photocatalytic filter 6, passing the interior of the photocatalytic filter 6 to reach the other of the surfaces of the light source 7. The photocatalyst 5 is thereby activated in the entire photocatalytic filter 6 (both surfaces and inner part).

The grease filter 34 is preferably installed at the upstream side of the photocatalytic filter 6 so that the majority of the oil portion in the oil smoke is collected beforehand by the grease filter 34. The grease filter 34 may be installed anywhere at the upstream side of the photocatalytic filter 6. Thereby, the amount of the oil portion reaching the photocatalytic filter 6 can be reduced, the reduction of the deodorizing effect in the photocatalytic filter 6 can be prevented, and the deodorizing effect can be improved. Moreover, the oil portion having reached the photocatalytic filter 6 can also be decomposed and removed by the photocatalytic reaction.

(Operational Advantage 1) The photocatalytic filter 6 using the photocatalyst 5 includes the filter substrate 4 made of the porous metal 11 (porous body made of metal). The porous metal 11 is a new metallic material having a sponge-like interior structure made of a metal or alloy having continuous air holes (pores) of a three-dimensional mesh structure throughout the entire structure. The porous metal 11 is relatively light with required strength, and can also be provided with the necessary heat or fire resistance.

In contrast, the existing photocatalytic filter 6 has used porous ceramics on the filter substrate 4. However, the porous ceramics are expensive and relatively heavy, and easily broken. Accordingly, the porous ceramics have to be handled with care and are easily broken when dropping them when handling, for example.

On the other hand, by changing the filter substrate 4 to the porous metal 11, the photocatalytic filter 6 can be provided at a lower cost. Moreover, because the porous metal 11 is light and sturdy, it does not have to be handled with care, unlike the porous ceramics. Furthermore, the photocatalytic filter 6 can be kept in a robust state (good maintenance) without damage due to the prevention of the breakage due to dropping or the like. Accordingly, costs of the deodorizing apparatus 1 and the photocatalytic filter 6 can be reduced, and the handling of the photocatalytic filter 6 can be improved.

Moreover, compared to the porous ceramics, the porous metal 11 is easily manufactured and available, hence can be easily and freely used as the filter substrate 4 of the photocatalytic filter 6. As mentioned above, since the porous metal 11 is light compared to the porous ceramics, the photocatalytic filter 6 itself and the deodorizing apparatus 1 using the photocatalyst 5 can be made light, and transporting and handling of the photocatalytic filter 6 and the deodorizing apparatus 1 can be improved due to the lighter weight thereof, hence has better convenience. Accordingly, the deodorizing apparatus 1 using the photocatalyst 5 easily has the potential for wide deployment and distribution both domestically and internationally.

Moreover, the porous metal 11 is easily manufactured and machined compared to the porous ceramics, and accordingly, can be freely formed in relatively any shape and size. Therefore, by using the porous metal 11, the lighter and bigger, photocatalytic filter 6 can be produced with fewer average cell number C in accordance with the objects of deodorization and application in such a way that the conventional porous ceramics cannot be achieved.

On the other hand, to improve the deodorizing effect of the deodorizing apparatus 1, the malodorous components in the cooking gas should have more opportunities to contact the photocatalyst 5 of the photocatalytic filter 6, or there should have opportunities to contact the photocatalyst 5 of the photocatalytic filter 6 as many as possible.

However, increasing the opportunities for the malodorous components to contact the photocatalyst 5 results in increased pressure loss of the photocatalytic filter 6. Therefore, in the photocatalytic filter 6, the pressure loss needs to be lowered as much as possible while increasing the contact opportunities between the malodorous components and the photocatalyst 5 (specifically, improve deodorizing effect). Thus, by optimizing the contact opportunities and the pressure loss, a compact and high-performing photocatalytic filter 6 is simultaneously obtainable.

Therefore, in the present embodiment, the product (t×C) of the porous metal 11 is set to be from 100 or more to 400 or less, where t is the thickness of the porous metal 11 and C is the average cell number per inch of the porous metal 11. Setting the product (t×C) of the thickness t and the average cell number C of the porous metal 11 to be from 100 or more to 400 or less makes it possible to optimize the contact opportunity and the pressure loss. Hence, the photocatalytic filter 6 using the porous metal 11 as the filter substrate 4 can be put into practical use.

Accordingly, by using the porous metal 11 as the filter substrate 4, the photocatalytic filter 6 can be optimized, and the pressure loss of the photocatalytic filter 6 can be suppressed. The untreated gas 3a then permeates substantially equally throughout the entire region of the porous metal 11, and the contact opportunity and/or the contact area of the catalyst supported onto the photocatalytic filter 6 with the untreated gas 3a (containing malodorous components therein) can be increased (deodorizing effect can be improved). Therefore, a new high-performing photocatalytic filter 6 with a good balance between the deodorizing effect and the pressure loss (specifically, a high deodorizing effect and a low-pressure loss) can replace the ceramic filter presently in use can be obtained.

Moreover, by using the porous metal 11 as the filter substrate 4 of the photocatalytic filter 6, the performance of the photocatalytic filter 6, with the obtainable toluene removal rate of 85% or more (as in the experimental results stipulated in JIS R 1701-3), can be equally exhibited throughout the entire region of the photocatalytic filter 6, and the efficient operation of the entire photocatalytic filter 6 can be realized. As a result, the deodorizing apparatus 1 can be made just high-performing and compact enough for the entire photocatalytic filter 6 to operate efficiently.

Further, the configuration where the product (t×C) of the thickness t and the average cell number C of the porous metal 11 is from 100 or more to 400 or less is specified. Thereby, objective selection criteria for the porous metal 11 are obtainable when adopting the porous metal 11 as the filter substrate 4 of the photocatalytic filter 6.

Subsequently, when designing the deodorizing apparatus 1, the most suitable porous metal 11 in accordance with the specific scale and the object of the deodorizing apparatus 1 can be quickly and certainly designated or selected to easily manufacture the photocatalytic filter 6. Accordingly, the effort and cost required to manufacture the photocatalytic filter 6 can be reduced.

(Operational Advantage 2) The porous metal 11 may also be formed of at least one or more materials selected from a group consisting of nickel (Ni), silver (Ag), copper (Cu), aluminum (Al), nickel-chrome, nickel-tin, and nickel-iron. Thus, the above-mentioned effects can be obtained by specifying the filter substrate 4 used in the photocatalytic filter 6 to be the porous metal 11 using at least one or more materials selected from a group consisting of nickel (Ni), silver (Ag), copper (Cu), aluminum (Al), nickel-chrome, nickel-tin, and nickel-iron. In addition, the specific criteria can be set with respect to the porous metal 11 for producing the photocatalytic filter 6 with stable quality and performance, and accordingly, the photocatalytic filter 6 can be provided as a highly reliable finished product with the desired deodorizing effect.

Moreover, the photocatalytic filter 6 can be easily produced by selecting the porous metal 11 with the most suitable material from several types of commercially available porous metals 11 in accordance with the specific objects of deodorization and the application of the deodorizing apparatus 1. Furthermore, it can also be expected that the function for promoting the catalytic activity by the porous metal 11 itself can be obtained by using the porous metal 11 made of any of the above-listed materials in the photocatalytic filter 6.

(Operational Advantage 3) The porous metal 11 may also contain nickel in the material. Thus, by designating the material of the filter substrate 4 used in the photocatalytic filter 6 to be the porous metal 11 containing nickel, the above-mentioned effects can be obtained. In addition, the specific criteria can be set with respect to the porous metal 11 for producing the photocatalytic filter 6 with stable quality and performance, and accordingly, the photocatalytic filter 6 can be provided as a highly reliable finished product with the desired deodorizing effect.

Moreover, nickel is a metal with a variety of characteristics such as high corrosion resistance, excellent durability, high strength in high and low temperatures, as well as having a function as a catalyst. Therefore, by containing nickel as a material in the porous metal 11, the filter substrate 4 becomes highly functional and a high-performing photocatalytic filter 6 is thus obtainable.

(Operational Advantage 4) The porous metal 11 may be configured so that the transmittance of the ultraviolet light 8*a* is 8% or less. Thus, by designating the transmittance of the ultraviolet light 8*a* in the porous metal 11 used in the photocatalytic filter 6 to be 8% or less, the above-mentioned effects can be obtained. In addition, the specific criteria can be set with respect to the porous metal 11 for producing the photocatalytic filter 6 with stable quality and performance, and accordingly, the photocatalytic filter 6 can be provided as a highly reliable finished product with the desired deodorizing effect.

It is moreover clear that the porous metal 11 has the transmittance of 8% or less for the ultraviolet light 8*a* transmittance. Thereby, the amount of the ultraviolet light 8*a* transmitted through the photocatalytic filter 6 and leaking to the opposite side can be reduced, and thus it can be ensured that more ultraviolet light 8*a* is used in the activation of the photocatalyst 5 in the interior of photocatalytic filter 6 (i.e., ultraviolet light 8*a* is more efficiently used).

Moreover, by checking the transmittance of the ultraviolet light 8*a*, e.g., during manufacturing, the photocatalytic filter 6 using the porous metal 11 can be easily inspected, and thus it can be determined whether the photocatalytic filter 6 has been appropriately finished. Further, by checking the transmittance of the ultraviolet light 8*a*, e.g., during maintenance, it can be easily judged whether the photocatalytic filter 6 is being kept in an optimal state.

(Operational Advantage 5) Titanium oxide may be used as the photocatalyst 5. Thus, by designating the photocatalyst 5 used in the photocatalytic filter 6, which uses the porous metal 11 in the filter substrate 4, to be titanium oxide, the above-mentioned effects can be obtained. In addition, the specific criteria can be set for producing the photocatalytic filter 6 with stable quality and performance, and accordingly, the photocatalytic filter 6 can be provided as a highly reliable finished product with the desired deodorizing effect.

Moreover, by specifying the photocatalyst 5 as titanium oxide, a novel photocatalytic filter 6 where titanium oxide, which is effective for deodorization, is fixed to the porous metal 11 as the photocatalyst 5 can be obtained.

(Operational Advantage 6) The photocatalyst 5 may have an average particle diameter in a range from 1 nm or more to 100 nm or less. Thus, by designating the average particle diameter of the photocatalyst 5 to range from 1 nm or more to 100 nm or less, wherein the photocatalyst 5 is used in the photocatalytic filter 6 which uses the porous metal 11 in the filter substrate 4, the above-mentioned effects can be obtained. In addition, the specific criteria can be set for producing the photocatalytic filter 6 with stable quality and performance, and accordingly, the photocatalytic filter 6 can be provided as a highly reliable finished product with the desired deodorizing effect.

Moreover, by using the photocatalyst 5 with the average particle diameter in a range from 1 nm or more to 100 nm or less, the high-performing photocatalytic filter 6, in which the photocatalyst 5 having the average particle diameter that provides the most effective deodorizing function is fixed to the porous metal 11, can be obtained.

(Operational Advantage 7) The support amount of the photocatalyst 5 for the filter substrate 4 may be from 1 g to 2.5 g per area of 50 mm×100 mm. Thus, by designating the support amount of the photocatalyst 5 for the porous metal 11, which is used in the filter substrate 4 of the photocatalytic filter 6, to be from 1 g to 2.5 g per area of 50 mm×100 mm, the above-mentioned effects can be obtained. In addition, the specific criteria can be set for producing the photocatalytic filter 6 with stable quality and performance, and accordingly, the photocatalytic filter 6 can be provided as a highly reliable finished product with the desired deodorizing effect.

Moreover, by designating the support amount of the photocatalyst 5 to be from 1 g to 2.5 g per area of 50 mm×100 mm, the novel photocatalytic filter 6, in which the photocatalyst 5 with the optimal amount for deodorization is fixed to the porous metal 11, can be obtained.

(Operational Advantage 8) The porous metal 11 may have a flat planar shape. Thus, by designating the shape of the porous metal 11, which is used in the filter substrate 4 of the photocatalytic filter 6, to be the flat planar shape, the above-mentioned effects can be obtained. In addition, the specific criteria can be set with respect to the porous metal 11 for producing the photocatalytic filter 6 having stable quality and performance, as well as the shape effective to the deodorization and easier to use. Accordingly, the photocatalytic filter 6 can be provided as a highly reliable finished product with the desired deodorizing effect.

Moreover, the porous metal 11 of the flat planar shape can be relatively easily machined and formed. Also, the photocatalytic filter 6 using the porous metal 11 with the flat planar shape can be relatively easily installed at the exhaust duct 2 and can be used as-is in the existing deodorizing apparatus 1. Furthermore, the photocatalytic filter 6 of the flat planar shape is of a shape that easily transmits the untreated gas 3*a*. Accordingly, the malodorous components in the untreated gas 3*a* may have greater contact with the photocatalyst 5 supported on the photocatalytic filter 6.

(Operational Advantage 9) According to the deodorizing apparatus 1 of the present embodiment, the effects similar to those of the photocatalytic filter 6 can be obtained.

The invention claimed is:

1. A photocatalytic filter comprises:
a filter substrate, the filter substrate being a porous metal; and
a photocatalyst fixed to the filter substrate, the photocatalyst comprising particles consisting of titanium oxide;
wherein a thickness t (mm) of the porous metal ranges from about 10 to about 15 and an average cell number per inch C (ppi) of the porous metal ranges from about 9 to about 25, provided that a product (t×C) of the thickness t and the average cell number C ranges from 100 to 400.

2. The photocatalytic filter according to claim 1, wherein the porous metal is formed of at least one or more materials selected from a group consisting of nickel, silver, copper, aluminum, nickel-chrome, nickel-tin, and nickel-iron.

3. The photocatalytic filter according to claim 1, wherein the porous metal contains nickel in the material.

4. The photocatalytic filter according to claim 1, wherein the porous metal has a transmittance of 8% or less for ultraviolet light.

5. The photocatalytic filter according to claim 1, wherein the photocatalyst has an average particle diameter in a range from 1 nm or more to 100 nm or less.

6. The photocatalytic filter according to claim 1, wherein an amount of the photocatalyst supported onto the filter substrate is from 1 g to 2.5 g per area of 50 mm×100 mm of a flat planar shape.

7. The photocatalytic filter according to claim 1, wherein the porous metal has a flat planar shape.

8. A deodorizing apparatus comprising the photocatalytic filter according to claim 1 and a light source.

9. The photocatalytic filter according to claim 1, wherein the titanium dioxide comprises anatase-type titanium dioxide.

* * * * *